US012721551B2

(12) United States Patent
Shinozaki et al.

(10) Patent No.: US 12,721,551 B2
(45) Date of Patent: Sep. 1, 2026

(54) METHOD FOR ELECTROCHEMICALLY MEASURING OXIDOREDUCTASE USING A BIOSENSOR, AND BIOSENSOR USED THEREIN

(71) Applicant: ARKRAY, Inc., Kyoto (JP)

(72) Inventors: Kotaro Shinozaki, Kyoto (JP); Misaki Oga, Kyoto (JP); Toshiyuki Mikami, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 302 days.

(21) Appl. No.: 18/185,305

(22) Filed: Mar. 16, 2023

(65) Prior Publication Data

US 2023/0293059 A1 Sep. 21, 2023

(30) Foreign Application Priority Data

Mar. 17, 2022 (JP) ................................ 2022-042572

(51) Int. Cl.
*A61B 5/145* (2006.01)
*A61B 5/1486* (2006.01)

(52) U.S. Cl.
CPC ........ *A61B 5/14532* (2013.01); *A61B 5/1486* (2013.01)

(58) Field of Classification Search
CPC ... A61B 5/145; A61B 5/14532; A61B 5/1486; C12Q 1/004; C12Q 1/006; C12Q 1/26;
(Continued)

(56) References Cited

U.S. PATENT DOCUMENTS 5,108,564 A 4/1992 Szuminsky et al.
5,122,244 A * 6/1992 Hoenes .................. C12Q 1/004
205/777.5

(Continued)

FOREIGN PATENT DOCUMENTS

JP H03-293556 A 12/1991
JP 2651278 B2 9/1997

(Continued)

OTHER PUBLICATIONS

The extended European search report mailed by the European Patent Office on Aug. 8, 2023, which corresponds to European Patent Application No. 23162446.1-1001 and is related to U.S. Appl. No. 18/185,305.

(Continued)

*Primary Examiner* — Luan V Van
(74) *Attorney, Agent, or Firm* — Studebaker Brackett PLLC

(57) ABSTRACT

A method for electrochemically measuring an amount of an oxidoreductase using a biosensor which includes a conductive part including two or more electrodes, and a reagent layer that is in contact with the conductive part and includes a substrate of the oxidoreductase and two or more types of mediators. A first mediator transfers, to a second mediator, electrons generated by a reaction between the substrate and the oxidoreductase, and a second mediator transfers, to the electrodes, the electrons transferred from the first mediator. The method includes bringing a sample containing an oxidoreductase into contact with a reagent layer; performing incubation for a predetermined period of time after the contact, to cause the second mediator to accumulate electrons; applying a voltage across the electrodes after the incubation; measuring an electric signal generated by the
(Continued)

voltage application; and calculating an amount of the oxidoreductase based on the electric signal.

12 Claims, 9 Drawing Sheets

(58) Field of Classification Search
CPC ............... G01N 27/3272; G01N 27/26; G01N 27/3271; G01N 27/48
See application file for complete search history.

(56) References Cited

U.S. PATENT DOCUMENTS

| | | | | |
|---|---|---|---|---|
| 5,243,516 | A | 9/1993 | White | |
| 5,366,609 | A | 11/1994 | White et al. | |
| 6,284,125 | B1 | 9/2001 | Hodges et al. | |
| 2009/0068754 | A1 | 3/2009 | Wu et al. | |
| 2012/0135509 | A1* | 5/2012 | Hall | C12Q 1/001 422/82.01 |
| 2015/0101929 | A1* | 4/2015 | Jung | G01N 33/5438 435/26 |
| 2019/0233870 | A1 | 8/2019 | Buck et al. | |
| 2024/0011990 | A1* | 1/2024 | Sankar | G01N 33/54386 |

FOREIGN PATENT DOCUMENTS

| | | | |
|---|---|---|---|
| JP | 2702286 | B2 | 1/1998 |
| JP | 2901678 | B2 | 6/1999 |
| JP | 2007-225305 | A | 9/2007 |
| JP | 4018748 | B2 | 12/2007 |
| JP | 5244116 | B2 | 7/2013 |
| WO | 89/08713 | A1 | 9/1989 |
| WO | 94/29703 | A1 | 12/1994 |
| WO | 97/00441 | A1 | 1/1997 |
| WO | 2008/051742 | A2 | 5/2008 |

OTHER PUBLICATIONS

Yu Xiang et al., "Using personal glucose meters and functional DNA sensors to quantify a variety of analytical targets", Nature Chemistry, 2012, 3(9): 697-703.

Tian Lan et al., "Detection of Protein Biomarker Using a Blood Glucose Meter", Methods Mol Biol. 2015, 1256: 99-109.

Naveen K. Singh et al., "Hitting the diagnostic sweet spot: Point-of-care SARS-CoV-2 salivary antigen testing with an off-the-shelf glucometer", Biosensors and Bioelectronics, 2021, 180, 113111.

Tian Lan et al., "Transforming the blood glucose meter into a general healthcare meter for in vitro diagnostics in mobile health", Biotechnology Advances, 2016, 34(3): 331-341.

Jinhee Lee et al., Electrochemistry, 2015, 83(12), 1085-1090 with partial English machine translation.

Yoshihiko Nonaka et al., "Electrochemical Detection of Vascular Endothelial Growth Factor with Aptamer Sandwich", Electrochemistry, 2012, 80(5) 363-366.

Koichi Abe et al., "Electrochemical Detection of Vascular Endothelial Growth Factor by an Aptamer-Based Bound/Free Separation System ", Electrochemistry, 2012, 80(5), 348-352.

Nasa Savory et al., "Development of aptamer based biosensors for electrochemical detection of pathogenic *E. coli*", Urakami Foundation memoirs, 2014, vol. 21, p. 136-p. 142.

* cited by examiner

FIG. 6A
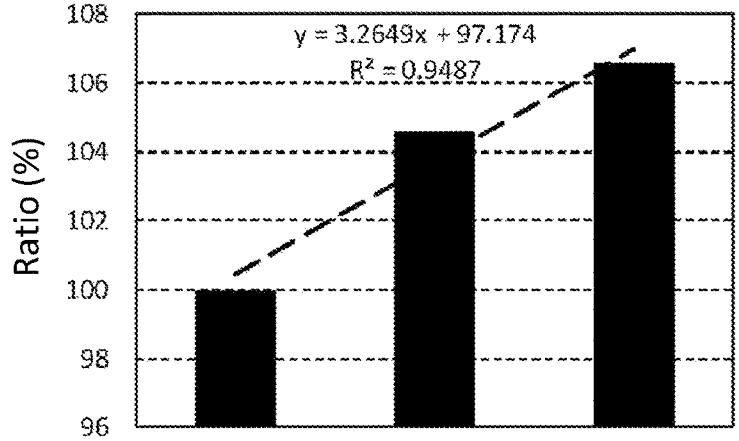
FIG. 6B
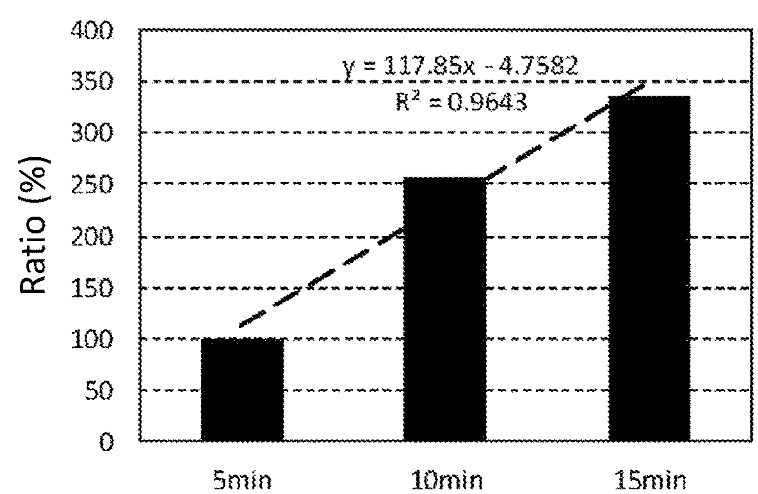
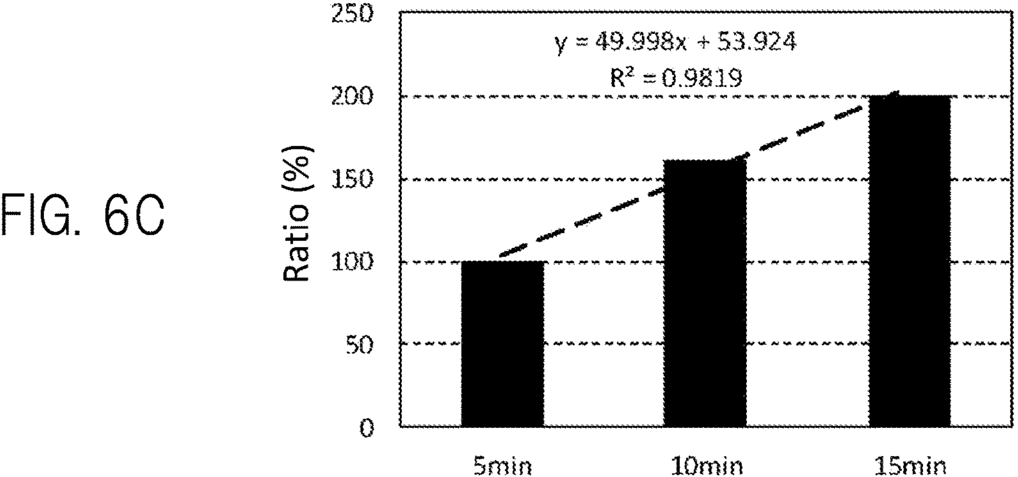
FIG. 6C

Second measurement

Response (nA)

12000
10000
8000
6000
4000
2000
0

| GDH_55.56 nM | GDH_5.56 nM | GDH_0.56 nM |
|---|---|---|
| Incubation time 1min | Incubation time 3min | Incubation time 5min |

METHOD FOR ELECTROCHEMICALLY MEASURING OXIDOREDUCTASE USING A BIOSENSOR, AND BIOSENSOR USED THEREIN

CROSS-REFERENCE TO RELATED APPLICATION

This application claims benefit of priority to Japanese Patent Application No. 2022-042572, filed Mar. 17, 2022, the entire content of which is incorporated herein by reference.

BACKGROUND

Technical Field

The present disclosure relates to a method for electrochemically measuring an amount of an oxidoreductase using a biosensor, and to a biosensor used in this method.

Background Art

A biosensor is a molecular measuring device using a detection unit in which a biological material such as an enzyme is arranged and a transducer (signal conversion device) such as electrodes. The biosensor is used for measuring various biological analysis objects such as glucose in a living body.

Electrochemical measurement with an enzyme is generally performed as a method for measuring a concentration of glucose using a biosensor. As one type of method with which a concentration of glucose can be measured with accuracy, various methods that apply the Cottrell equation have been reported (JP-A-3(1991)-293556, Japanese Patent No. 2651278, Japanese Patent No. 2702286, Japanese Patent No. 2901678, Japanese Patent No. 4018748, Japanese Patent No. 5244116). The Cottrell equation is one of the diffusion equations that depend on the electrode size and shape. As is well known, since the thickness of an electrode used in a biosensor such as a glucose sensor is relatively small as compared with the range in which diffusion occurring with electron transfer occurs (up to several hundreds of micrometers), the current response arising when a potential is applied to an electrode is not constant, and attenuates in inverse proportion to a square root of time (attenuates in proportion to $t^{-1/2}$) according to the Cottrell equation. Japanese Patent No. 2901678 discloses a method in which, in order to measure an amount of an analysis object while preventing a difference from occurring in measured values depending on a user, the analysis object and a reagent (oxidizer and oxygen, etc.) are mixed in a measurement cell having electrodes to react with each other, incubation is performed until the end of the enzyme reaction, and then a voltage is applied to the electrodes to measure a Cottrell current.

On the other hand, for the Cottrell current (having attenuation in line with the Cottrell equation) to be established, it is necessary that there should be no substantial change in the concentration of the materials after the application of a voltage, that is, the enzyme reaction should be substantially complete. Therefore, the method disclosed in Japanese Patent No. 2901678 has a problem that it is necessary to ensure a certain reaction time, which means that the method requires time before the measurement. Accordingly, Japanese Patent No. 5244116 proposes to measure glucose by using an electrochemical process without Cottrell attenuation. Cottrell attenuation has an attenuation coefficient of −0.5 (constant). Japanese Patent No. 5244116 discloses a configuration in which an attenuation coefficient in such a short reaction (incubation) time that does not allow the enzyme reaction to finish is initially determined, and a concentration of an analysis object in a sample is determined based on the attenuation coefficient and an output signal having transition attenuation.

In recent years, a method for electrochemically measuring a concentration of a biological material other than glucose has been reported (Yu Xiang et al., Nature Chemistry, 2012, 3(9): 697-703, Tian Lan et al., Methods Mol Biol. 2015, 1256, 99-109, Naveen K. Singh et al., Biosensors and Bioelectronics, 2021, 180, 113111, Tian Lan et al., Biotechnology Advances, 2016, 34(3) 331-341, Jinhee Lee et al., Electrochemistry, 2015, 83(12) 1085-1090, Yoshihiko Nonaka et al., Electrochemistry, 2012, 80(5) 363-366, Koichi Abe et al., Electrochemistry, 2012, 80(5) 348-352, Nasa Savory et al., Urakami Foundation memoirs, 2014, Vol. 21 136-142). Yu Xiang et al, Tian Lan et al. (2015), Naveen K. Singh et al., and Tian Lan et al. (2016) disclose a configuration in which sucrose is converted by an oxidoreductase into glucose, and is measured by a glucose meter (Blood Glucose Meter, BGM) or the like. On the other hand, however, this configuration has a problem that, when an analysis object in a sample has a lower concentration relative to that of glucose, or an extremely low concentration, a sufficient sensitivity cannot be obtained as compared with a case of measuring glucose. In view of this, a method of modifying electrodes, a method of localizing multiple electron transfer enzymes, and the like, for enhancing the sensitivity are reported in the disclosure of Jinhee Lee et al. A method that uses glucose dehydrogenase (GDH) as a detection enzyme to measure a response current of GDH and converts a concentration of an analysis object into GDH, for measuring a concentration of a vascular endothelium cell growth factor (VEGF) in blood is reported in the disclosures of Yoshihiko Nonaka et al. and Koichi Abe et al.

SUMMARY

In the process of earnest research with a view to providing a method capable of electrochemically measuring a concentration of a biological material using a biosensor, the present inventors found the following new problem: when an analysis object having a low or extremely low concentration is converted to an oxidoreductase by utilizing an aptamer, or the like so that an amount of the oxidoreductase is electrochemically measured, as disclosed in Yoshihiko Nonaka et al., Koichi Abe et al., and Nasa Savory et al., the response current generated is minute, which means that a sufficient sensitivity cannot be obtained. In addition, the present inventors also found that the mediator used in the methods of Yoshihiko Nonaka et al., Koichi Abe et al., and Nasa Savory et al. is of a single mediator, and a sufficient sensitivity cannot be obtained by a single-mediator-type biosensor.

The present disclosure, in one aspect, provides a method capable of electrochemically measuring an amount of an oxidoreductase with a high sensitivity, and provides a biosensor used in the measurement.

The present disclosure, as one aspect, relates to a method for electrochemically measuring an amount of an oxidoreductase using a biosensor. The biosensor includes a conductive part including two or more electrodes; and a reagent layer that is arranged in contact with the conductive part. The reagent layer includes a substrate of the oxidoreductase and two or more types of mediators, and the mediators include a first mediator and a second mediator. The first mediator is a mediator for transferring, to the second mediator, electrons generated by a reaction between the substrate and the oxidoreductase, and the second mediator is a mediator for transferring, to the electrodes, the electrons transferred from the first mediator. The method includes bringing a sample containing an oxidoreductase into contact with the reagent layer; performing incubation for a predetermined time after the contact, thereby causing the second mediator to accumulate the electrons; applying a voltage across the electrodes after the incubation; measuring an electric signal generated by the application of the voltage; and calculating an amount of the oxidoreductase based on the electric signal.

The present disclosure relates to, as another aspect, a method for electrochemically measuring an amount of an oxidoreductase using a biosensor. The biosensor includes a conductive part including two or more electrodes; and a reagent layer that includes a substrate of the oxidoreductase and two or more types of mediators, and is arranged in contact with the conductive part. The mediators include a first mediator and a second mediator, the first mediator being intended to transfer, to the second mediator, electrons generated by a reaction between the substrate and the oxidoreductase, and the second mediator being intended to transfer, to the electrodes, the electrons transferred from the first mediator. The method includes bringing a sample containing the oxidoreductase into contact with the reagent layer of the biosensor; applying a voltage across the electrodes after the contact (first application); measuring an electric signal generated by the first application (first measurement); calculating an incubation time based on the electric signal obtained by the first measurement; performing incubation for the incubation time thus calculated; applying a voltage across the electrodes after the incubation (second application); measuring an electric signal generated by the second application (second measurement); and calculating an amount of the oxidoreductase based on the electric signal obtained by the second measurement.

The present disclosure relates to, as another aspect, a biosensor for electrochemically measuring an oxidoreductase. The biosensor includes a conductive part including two or more electrodes; and a reagent layer that includes a substrate of the oxidoreductase and two or more types of mediators, and is arranged in contact with the conductive part. The mediators include a first mediator and a second mediator. The first mediator is intended to transfer, to the second mediator, electrons generated by a reaction between the substrate and the oxidoreductase, and the second mediator is intended to transfer, to the electrodes, the electrons transferred from the first mediator. The biosensor is intended to be used in the measuring method of the present disclosure.

With the present disclosure, in one aspect, it is possible to provide a method capable of electrochemically measuring an amount of an oxidoreductase with a high sensitivity, and to provide a biosensor used in the measurement.

BRIEF DESCRIPTION OF THE DRAWINGS

FIGS. TA to 1E illustrate steps of an exemplary method for manufacturing a biosensor in one embodiment of the present disclosure, in which schematic diagrams of the biosensor in the steps are shown, respectively;

FIGS. 6A to 6C are graphs showing exemplary results of Experiment Example 2, and the graphs show results of evaluation of the relationship between an incubation (electron storage) time and a ratio of response current, by performing incubation for 5 minutes, 10 minutes, or 15 minutes, using a reaction solution that contains a substrate (glucose), mediators (1-mPES and a ruthenium compound), and GDH (final concentration: 0.56 nM, 5.56 nM, or 55.56 nM);

DETAILED DESCRIPTION

Figure 1A:
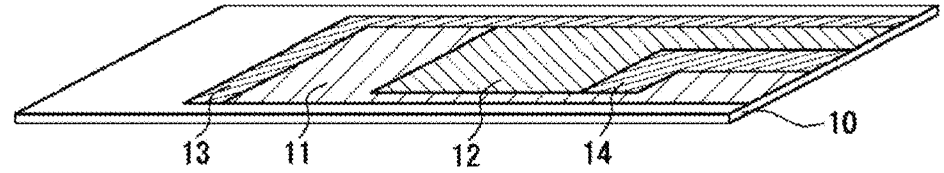

The present inventors have made earnest research with a view to providing a method capable of electrochemically measuring an amount of an oxidoreductase in a reaction solution with a high sensitivity, using a biosensor. In the process of the research, the present inventors confirmed that it is difficult for one mediator to satisfy both of the requirements of efficiently receiving electrons generated in a reaction between an oxidoreductase and a substrate, and continuously storing the electrons thus received, which means that it is impossible to obtain a sufficient sensitivity with a single mediator. Then, the present inventors found the following: an amount of the oxidoreductase can be measured electrochemically with a high sensitivity by using, in combination as mediators provided in a biosensor, a mediator (second mediator) having a high electron storage capability, and a mediator (first mediator) that can rapidly receive electrons generated in a reaction between an oxidoreductase and a substrate and transfer the electrons to the second mediator, in order to promote the oxidoreductase reaction between the substrate and the oxidoreductase and to cause the second mediator to store the electrons generated in the reaction. The inventors arrived at the method of the present disclosure based on these findings.

Differences between the measuring method of the present disclosure and that of a common biosensor such as glucose measuring devices disclosed in Patent Documents mentioned in the above section of "Description of Related Art" (JP-A-3(1991)-293556, Japanese Patent No. 2651278, Japanese Patent No. 2702286, Japanese Patent No. 2901678, Japanese Patent No. 4018748, and Japanese Patent No. 5244116) are as follows. In a common biosensor, an "oxidoreductase" and a "mediator" are provided in sufficient amounts with respect to a concentration range of an analyte (glucose) in a sample so that a reaction of the analyte (glucose) and the oxidoreductase, as well as transfer of electrons accompanying the reaction, should be performed smoothly. In a common glucose sensor, quantification of glucose is performed by causing an analyte (glucose) and an oxidoreductase to react in a sensor having electrodes provided with sufficient amounts of the "oxidoreductase" and a "mediator", and measuring a value of a response current generated by electrons that are released from glucose in this reaction and are transferred via the mediator to the electrodes. In other words, when a voltage is applied, an enzyme reaction between the analyte and the oxidoreductase is substantially complete, or the enzyme reaction has proceeded to such an extent that the concentration of the analyte can be determined, which is a state in which the electron transfer from the analyte (glucose) to the mediator is substantially complete or has sufficiently proceeded.

In contrast, in the measuring method of the present disclosure, an "oxidoreductase" is a target to be measured, and a biosensor is provided with at least a "substrate of the oxidoreductase, and a "mediator (second mediator)" for storing electrons generated in the reaction. In other words, the biosensor used in the measuring method of the present disclosure is not substantially provided with a sufficient amount of the oxidoreductase. In the measuring method of the present disclosure, the oxidoreductase as a target to be measured and the substrate are caused to react for a predetermined time, and electrons generated by the reaction are stored in the second mediator via the first mediator, and then, an electric signal (value of response current) generated by applying a voltage across the electrodes after the storage is measured. That is, in the measuring method of the present disclosure, the reaction between the oxidoreductase as a target to be measured and the substrate is performed by incubation during a predetermined period of time within a time range in which the substrate is not exhausted. In other words, the incubation is finished at a certain predetermined timing within a time range at which the state is such that only a proportion of the substrate has reacted with the oxidoreductase. An amount of the oxidoreductase is then calculated based on an electric signal obtained as a result of application of a voltage at the predetermined timing. In this point, the measuring method of the present disclosure has a difference from the conventional method using the common biosensor. In other words, according to the measuring method of the present disclosure, a continuous reaction between an oxidoreductase and a substrate is performed, the electrons generated by the reaction are rapidly received by the first mediator and transferred to the second mediator, and the electrons are stored by the second mediator, whereby an amount of the oxidoreductase in the reaction solution can be measured at a high detection sensitivity, even when the oxidoreductase has an extremely low concentration, for example, in a pM order (for example, 1 to 10 pg/L). In addition, as the reaction between the oxidoreductase and the substrate proceeds time-dependently, the reaction amount, that is, the amount of electrons transferred, depends on the amount of the oxidoreductase. Therefore, by setting the time for incubation to a predetermined period of time, the amount of the oxidoreductase can be calculated.

[Measuring Methods]

The present disclosure, in one aspect, relates to a method for electrochemically measuring an amount of an oxidoreductase using a biosensor. The measuring method of the present disclosure, in one or a plurality of embodiments, uses a biosensor including at least the following: two or more types of mediators including a first mediator and a second mediator that are described below; and a substrate of an oxidoreductase. The method includes performing incubation for a predetermined period of time for storing electrons generated in a continuous reaction between the substrate and the oxidoreductase via the first mediator into the second mediator, followed by applying a voltage and measuring an electric signal generated thereby.

The phrase of "storing electrons . . . into the second mediator" in the present disclosure, in one or a plurality of embodiments, can be rephrased in that the second mediator, receiving electrons, is converted into the reduced form, and the second mediator in the reduced form accumulates the electrons.

The "electrochemical measuring method" in the present disclosure is a measuring method using electrochemical techniques, and in one or a plurality of embodiments, examples of this method include a measuring method for measuring a measurement object (oxidoreductase) in a reaction solution by converting a change corresponding to its concentration into an electric signal on electrodes and outputting the same. In one or a plurality of embodiments, examples of the electrochemical techniques include chronoamperometry, chronocoulometry, and cyclic voltammetry. In one or a plurality of embodiments, examples of the electric signal in the present disclosure include a value of response current with respect to an applied voltage, a response voltage value with respect to an applied voltage, and the like.

[Biosensor]

The biosensor used in the method of the present disclosure includes a conductive part including two or more electrodes, and a reagent layer arranged in contact with the conductive part. The reagent layer includes a substrate of an oxidoreductase, and two or more types of mediators, and the mediators include at least a first mediator and a second mediator, the first mediator being intended to transfer, to the second mediator, electrons generated by a reaction between the substrate and the oxidoreductase, the second mediator being intended to transfer, to the electrodes, the electrons transferred from the first mediator. The biosensor used in the method of the present disclosure, in one or a plurality of embodiments, includes a base material, and the conductive part and the reagent layer are arranged on the base material.

[Oxidoreductase]

Examples of the oxidoreductase, in one or a plurality of embodiments, include glucose dehydrogenase (GDH), glucose oxidase (GOD), cholesterol oxidase, quinohem ethanol dehydrogenase, sorbitol dehydrogenase, D-fructose dehydrogenase, D-glucoside-3-dehydrogenase, cellobiose dehydrogenase, lactate oxidase (LOD), lactate dehydrogenase (LDH), and urinate dehydrogenase. The oxidoreductase, in one or a plurality of embodiments, may include flavin adenine dinucleotide (FAD), pyrroloquinoline quinone (PQQ), nicotinamide adenine dinucleotide (NAD), or nicotinamide adenine dinucleotide phosphate (NADP), as a co-enzyme (also referred to as a catalyst sub-unit, or a catalyst domain). In one or a plurality of embodiments, examples of the oxidoreductase containing a co-enzyme include FAD-GDH, PQQ-GDH, NAD-GDH, and NADP-GDH. Examples of the oxidoreductase, in one or a plurality of embodiments, include *Aspergillus oryzae*-type FAD-GDH (flavin adenine dinucleotide-dependent glucose dehydrogenase, or flavin adenine dinucleotide-linked glucose dehydrogenase). As the *Aspergillus oryzae*-type FAD-GDH, in one or a plurality of embodiments, those disclosed in JP-A-2013-083634 can be used. The contents of the foregoing document are incorporated herein by reference as a part of the present disclosure.

[Substrate]

The substrate can be determined appropriately depending on the type of the oxidoreductase as a target to be measured. Examples of the substrate, in one or a plurality of embodiments, include glucose, cholesterol, sorbitol, D-fructose, cellobiose, lactic acid, and uric acid. In one or a plurality of embodiments, a sufficient amount of the substrate is arranged in the reagent layer of the biosensor.

With a view to increasing the measurement sensitivity by promoting the reaction between the substrate and the oxidoreductase while preventing the reaction from becoming rate-controlling, an amount of the substrate in the reagent layer (per 1 $cm^3$ of the reagent layer) is 4.4 nmol or more, preferably 8.8 nmol or more, 13.2 nmol or more, 17.6 nmol or more, or 22.0 nmol or more, and more preferably 26.4 nmol or more, in one or a plurality of embodiments. The upper limit of the amount of the substrate in the reagent layer (per 1 $cm^3$ of the reagent layer) is not particularly limited, and is 220 nmol or less, 176 nmol or less, 132 nmol or less, 88 nmol or less, or 44 nmol or less, in one or a plurality of embodiments. In one or a plurality of particularly non-limiting embodiments, the amount of the substrate in the reagent layer (per 1 $cm^3$ of the reagent layer) is 4.4 nmol to 220 nmol, 8.8 nmol to 176 nmol, or 26.4 nmol to 88 nmol.

With a view to increasing the measurement sensitivity by promoting the reaction between the substrate and the oxidoreductase while preventing the reaction from becoming rate-controlling, an amount of the substrate in the reagent layer (concentration of the substrate during incubation), as a content of the same with respect to an amount of a sample brought into contact with the reagent layer (concentration of the substrate during incubation), is 10 mM or more, preferably 20 mM or more, 30 mM or more, 40 mM or more, or 50 mM or more, and more preferably 60 mM or more, in one or a plurality of embodiments. The upper limit of the amount of the substrate in the reagent layer (concentration of the substrate during incubation) is not particularly limited, and is 500 mM or less, 400 mM or less, 300 mM or less, 200 mM or less, or 100 mM or less, in one or a plurality of embodiments.

The concentration of the substrate during incubation may be determined depending on the amount of the oxidoreductase as a target to be measured, in one or a plurality of embodiments. In one or a plurality of particularly non-limiting embodiments, when the amount of the oxidoreductase as a target to be measured (an amount predicted to be contained in a sample) is 0.01 nM to 60 nM, the concentration of the substrate during incubation is 10 mM or more, preferably 20 mM or more, 30 mM or more, 40 mM or more, or 50 mM or more, and more preferably 60 mM or more. In one or a plurality of particularly non-limiting embodiments, the amount of the substrate in the reagent layer (concentration of the substrate during incubation), as a content of the same with respect to an amount of a sample brought into contact with the reagent layer (concentration of the substrate during incubation) is 10 mM to 500 mM, 20 mM to 400 mM, or 60 mM to 100 mM.

An amount of a sample brought into contact with the reagent layer can be determined appropriately, and in one or a plurality of embodiments, it is about 1 μL to 20 μL.

[Mediator]

In one or a plurality of embodiments, examples of the mediator include ruthenium compounds, 1-methoxy-PES (1-methoxy-5-ethylphenazinium ethylsulfate, 1-mPES), 1-methoxy-PMS (1-methoxy-5-methylphenazinium methylsulfate, 1-mPMS), phenylenediamine compounds, quinone compounds, ferricyanide compounds, Coenzyme QO (2,3-dimethoxy-5-methyl-p-benzoquinone), AZURE A Chloride (3-amino-7-(dimethylamino)phenothiazin-5-ium chloride), Phenosafranin (3,7-diamino-5-phenylphenanzinium chloride), 6-aminoquinoxaline, and tetrathiafulvalene.

As the ruthenium compound, in one or a plurality of embodiments, a ruthenium compound that is present in a reaction system as an oxide-type ruthenium complex and functions as a mediator (electron transfer body) can be used. The type of a ligand of the ruthenium complex is not limited particularly. In one or a plurality of embodiments, examples of the ruthenium compound include an oxide-type ruthenium complex expressed by the following chemical formula:

$$[Ru(NH_3)_5X]^{n+}$$

X is, for example, $NH_3$, a halogen ion, CN, pyridine, nicotinamide, or $H_2O$, among which $NH_3$ or halogen ion is preferable. In one or a plurality of embodiments, examples of the halogen ion include $Cl^-$, $F^-$, $Br^-$, and I. "n+" in the chemical formula represents a valence of the oxide-type ruthenium (III) complex determined by the type of X. As the ruthenium complex, in one or a plurality of embodiments, those disclosed in JP-A-2018-013400 can be used. The contents of the foregoing document are incorporated herein by reference as a part of the present disclosure. In one or a plurality of embodiments, examples of the ruthenium compound include ruthenium hexamines such as $[Ru(NH_3)_6]^{2+}$ and $[Ru(NH_3)_6]^{3+}$. In one or a plurality of embodiments, examples of the ruthenium compound include $[Ru(NH_3)_6]Cl_3$.

In one or a plurality of embodiments, examples of the phenylenediamine compound include N,N-Dimethyl-1,4-phenylenediamine, and N,N,N',N'-tetramethyl-1,4-phenylenediaminedihydrochloride. In one or a plurality of embodiments, examples of the quinone compound include 1,4-naphthoquinone, 2-methyl-1,4-naphthoquinone (VK3), 9,10-penzoquinone, 1,2-naphthoquinone, p-xyloquinone, methylbenzoquinone, 2,6-dimethylbenzoquinone, sodium1, 2-naphthoquinone-4-sulfonate, 1,4-anthraquinone, tetramethylbenzoquinone, and thymoquinone. In one or a plurality of embodiments, examples of the ferricyanide compound include calcium ferricyanide.

The combination of mediators used in the measuring method of the present disclosure may be appropriately selected depending on the type of the oxidoreductase as a target to be measured, the material of the electrodes in the conductive part, and the like, in one or a plurality of embodiments.

Examples of the combination of the first mediator and the second mediator in one or a plurality of particularly non-limiting embodiments include the combination of 1-mPES and the ruthenium compound, and the combination of 1-mPMS and the ruthenium compound. Regarding the combination of the mediators in one or a plurality of particularly non-limiting embodiments, examples of the combination include the combination of the first mediator of 1-mPES and the second mediator of the ruthenium compound. In one or a plurality of embodiments, examples of the ruthenium compound include ruthenium hexamines such as $[Ru(NH_3)_6]^{2+}$ and $[Ru(NH_3)_6]^{3+}$. In one or a plurality of embodiments, examples of the ruthenium compound include $[Ru(NH_3)_6]Cl_3$.

Examples of the combination of the first mediator and the second mediator in one or a plurality of particularly non-limiting embodiments include the combination of 1-mPES and $[Ru(NH_3)_6]Cl_3$, and the combination of 1-mPMS and $[Ru(NH_3)_6]Cl_3$. Regarding the combination of the mediators in one or a plurality of particularly non-limiting embodiments, examples of the combination include the combination of the first mediator of 1-mPES and the second mediator of $[Ru(NH_3)_6]Cl_3$.

The amounts of the first and second mediators in the reagent layer may be appropriately determined depending on the type of the oxidoreductase as a target to be measured, the types of the first and second mediators and the combination of these, the material of the electrodes in the conductive part, and the like, in one or a plurality of embodiments.

With a view to increasing the measurement sensitivity by preventing the transfer of electrons generated in the reaction between the substrate and the oxidoreductase from becoming rate-controlling, an amount of the first mediator in the reagent layer (per 1 $cm^3$ of the reagent layer) is 0.22 nmol or more, or 0.3 nmol or more, and preferably 0.35 nmol or more, 0.44 nmol or more, or 2.2 nmol or more, in one or a plurality of embodiments. The amount of the first mediator in the reagent layer (per 1 $cm^3$ of the reagent layer) may be 44 nmol or more, in one or a plurality of particularly non-limiting embodiments. The upper limit of the amount of the first mediator in the reagent layer (per 1 $cm^3$ of the reagent layer) is not particularly limited, and is 220 nmol or less, or 110 nmol or less, in one or a plurality of embodiments. In one or a plurality of particularly non-limiting embodiments, the amount of the first mediator in the reagent layer (per 1 $cm^3$ of the reagent layer) is 0.22 nmol to 220 nmol, 0.35 nmol to 220 nmol, or 44 nmol to 110 nmol.

With a view to reducing the production cost because a sufficient measurement sensitivity can be obtained even if the amount of the first mediator in the reagent layer is small as compared with that of the second mediator, the amount of the first mediator in the reagent layer is 44 nmol or less, 22 nmol or less, 17.6 nmol or less, 13.2 nmol or less, 8.8 nmol or less, or 4.4 nmol or less. In one or a plurality of particularly non-limiting embodiments, the amount of the first mediator in the reagent layer is 0.22 nmol to 44 nmol, 0.35 nmol to 22 nmol, or 2.2 nmol to 22 nmol.

With a view to increasing the measurement sensitivity by promoting the reaction between the substrate and the oxidoreductase while preventing the reaction from becoming rate-controlling, an amount of the first mediator in the reagent layer (concentration of the first mediator during incubation), as a content of the same with respect to an amount of a sample brought into contact with the reagent layer, is 0.5 mM or more, or 0.7 mM or more, and preferably 0.8 mM or more, 1 mM or more, or 5 mM or more, in one or a plurality of embodiments. The amount of the first mediator in the reagent layer (concentration of the first mediator during incubation) may be 100 mM or more, in one or a plurality of particularly non-limiting embodiments. The upper limit of the amount of the first mediator in the reagent layer is not particularly limited, and is 500 mM or less, or 250 mM or less, in one or a plurality of embodiments. In one or a plurality of particularly non-limiting embodiments, the amount of the first mediator in the reagent layer (concentration of the first mediator during incubation), as a content of the same with respect to an amount of a sample brought into contact with the reagent layer is 0.5 mM to 500 mM, 0.8 mM to 250 mM, or 5 mM to 250 mM.

With a view to reducing the production cost because a sufficient measurement sensitivity can be obtained even if the amount of the first mediator in the reagent layer is small as compared with that of the second mediator, the amount of the first mediator in the reaction layer is 100 mM or less, 50 mM or less, 40 mM or less, 30 mM or less, 20 mM or less, or 10 mM or less. In one or a plurality of particularly non-limiting embodiments, the amount of the first mediator in the reagent layer 0.5 mM to 100 mM, 0.8 mM to 50 mM, or 5 mM to 50 mM.

With a view to increasing the measurement sensitivity by making the second mediator capable of storing electrons while preventing the electron transfer from the first mediator from becoming rate-controlling, an amount of the second mediator in the reagent layer (per 1 $cm^3$ of the reagent layer) is 0.44 nmol or more, preferably 4.4 nmol or more, 22 nmol or more, 30.8 nmol or more, or 35.2 nmol or more, and more preferably 39.6 nmol or more, or 44 nmol or more, in one or a plurality of embodiments. The upper limit of the amount of the second mediator in the reagent layer (per 1 $cm^3$ of the reagent layer) is not particularly limited, and is 220 nmol or less, or 110 nmol or less, in one or a plurality of embodiments. In one or a plurality of particularly non-limiting embodiments, the amount of the second mediator in the reagent layer (per 1 $cm^3$ of the reagent layer) is 0.44 nmol to 220 nmol, 4.4 nmol to 110 nmol, or 39.6 nmol to 110 nmol.

With a view to increasing the measurement sensitivity by making the second mediator capable of storing electrons while preventing the electron transfer from the first mediator from becoming rate-controlling, an amount of the second mediator in the reagent layer (concentration of the second mediator during incubation), as a content of the same with respect to an amount of a sample brought into contact with the reagent layer, is 1 mM or more, preferably 10 mM or more, 50 mM or more, 70 mM or more, or 80 mM or more, and more preferably 90 mM or more, or 100 mM or more, in one or a plurality of embodiments. The upper limit of the amount of the second mediator in the reagent layer is not particularly limited, and is 500 mM or less, or 250 mM or less, in one or a plurality of embodiments. In one or a plurality of particularly non-limiting embodiments, the amount of the second mediator in the reagent layer (concentration of the second mediator during incubation), as a content of the same with respect to an amount of a sample brought into contact with the reagent layer is 1 mM to 500 mM, 10 mM to 250 mM, or 90 mM to 250 mM.

The reagent layer may contain components other than the substrate of the oxidoreductase and the mediators. Examples of the other component include a buffer, a surfactant, and a binder.

In one or a plurality of embodiments, examples of the buffer include a phosphate buffer, an amine-based buffer, and a buffer having a carboxyl group. In one or a plurality of embodiments, examples of the amine-based buffer include Tris (tris(hydroxymethyl)aminomethane), ACES (N-(2-Acetamido)-2-aminoethanesulfonic acid), CHES (N-Cyclohexyl-2-aminoethanesulfonic acid), CAPSO (3-(Cyclohexylamino)-2-hydroxy-1-propanesulfonic acid), TAPS (N-Tris(hydroxymethyl)methyl-3-aminopropanesulfonic acid), CAPS (N-Cyclohexyl-3-aminopropanesulfonic acid), Bis-Tris (Bis(2-hydroxyethyl)iminotris(hydroxymethyl)methane), TAPSO (2-Hydroxy-N-tris (hydroxymethyl)methyl-3-aminopropanesulfonic acid), TES (N-Tris(hydroxymethyl)methyl-2-aminoethanesulfonic acid), Tricine (N-[Tris(hydroxymethyl)methyl]glycine), and ADA (N-(2-Acetamido)iminodiacetic acid). In one or a plurality of embodiments, examples of the buffer having a carboxyl group include a citrate buffer, a phosphate citrate buffer, an acetic acid-sodium acetate buffer, a malic acid-sodium acetate buffer, a malonic acid-sodium acetate buffer, and a succinic acid-sodium acetate buffer. As the buffer, one type may be used alone, or two or more types may be used in combination. In one or a plurality of embodiments, the pH of the buffer is 6.0 to 8.0, and preferably 7.3 to 7.4.

In one or a plurality of embodiments, examples of the surfactant include tritonX-100 ((p-tert-octylphenoxy)polyethoxyethanol), Tween20 (polyoxyethylene sorbitan monolaurate), sodium dodecyl sulfate, perfluorooctanesulfonic acid, sodium stearate, alkylaminocarboxylic acid (or a salt thereof), carboxybetaine, sulfobetaine, and phosphobetaine. As the surfactant, one type may be used alone, or two or more types may be used in combination.

In one or a plurality of embodiments, examples of the binder include a resin binder and a layered inorganic compound. In one or a plurality of embodiments, examples of the resin binder include a butyral resin binder, and a polyester resin compound binder. As the layered inorganic compound, the layered inorganic compounds disclosed in WO2005/043146 can be used. In one or a plurality of embodiments, examples of the layered inorganic compound include a swelling clay mineral having an ion exchange capacity. In one or a plurality of embodiments, examples of the layered inorganic compound include bentonite, smectite, vermiculite, and synthetic fluoromica. As the binder, one type may be used alone, or two or more types may be used in combination.

In one or a plurality of embodiments, the reagent layer contains substantially no oxidoreductase. In one or a plurality of embodiments, the reagent layer contains substantially no oxidoreductase that reacts with the substrate contained in the reagent layer. In the present disclosure, "contains substantially no oxidoreductase" means that the amount of the oxidoreductase in the reagent layer (per 1 $cm^3$ of the reagent layer) is less than 0.1 U, less than 0.05 U, or less than 0.01 U, in one or a plurality of embodiments. In the present disclosure, "U" is a unit of an enzyme activity, and refers to an amount of an enzyme that reacts with 1 μmol of a substrate during 1 minute under optimum conditions.

[Conductive Part]

The conductive part includes two or more electrodes. The conductive part is an electrically conductive part. In one or a plurality of embodiments, the electrodes may be an electrode pair that includes a working electrode and a counter electrode, or may be an electrode pair of a three-electrode system that includes a working electrode, a counter electrode, and a reference electrode. In one or a plurality of embodiments, the conductive part may further include a detection electrode.

As the material for the electrodes, in one or a plurality of embodiments, conductive materials can be used. In one or a plurality of embodiments, examples of the conductive material include metal materials and carbon materials. In one or a plurality of embodiments, examples of the metal material include gold (Au), platinum (Pt), silver (Ag), ruthenium (Ru), palladium (Pd), and nickel (Ni) alloys. In one or a plurality of embodiments, examples of the nickel alloy include nickel-vanadium alloy, nickel-tungsten alloy, and nickel-ruthenium alloy. In one or a plurality of embodiments, examples of the carbon material include graphite, carbon nanotube, graphene, and mesoporous carbon.

In one or a plurality of embodiments, examples of the electrode include a thin film electrode formed by forming a film of a metal material on a base material. In one or a plurality of embodiments, examples of the film forming method include screen printing, physical vapor deposition (PVD, for example, sputtering), and chemical vapor deposition (CVD).

In one or a plurality of embodiments, the conductive part is formed on a base material. As the base material, in one or a plurality of embodiments, an insulating base material (insulating substrate) can be used. In one or a plurality of embodiments, examples of the material for the insulating substrate include thermoplastic resin, thermosetting resin, glass, ceramic, and paper. In one or a plurality of embodiments, examples of the thermoplastic resin include polyether-imide (PEI), polyethylene terephthalate (PET), and polyethylene (PE). Examples of the thermosetting resin include polyimide resin, and epoxy resin.

The measuring method of the present disclosure includes: bringing a sample containing an oxidoreductase into contact with a reagent layer in a biosensor; performing incubation for a predetermined period of time after the contact between the sample and the reagent layer, so as to cause a second mediator in the reagent layer to accumulate electrons generated by a reaction between the oxidoreductase and a substrate, via a first mediator; applying a voltage across electrodes in a conductive part in the biosensor after the incubation; measuring an electric signal generated by the voltage application; and calculating an amount of the oxidoreductase based on the electric signal measured.

The "performing incubation" in the present disclosure refers to performing an oxidation-reduction reaction between the oxidoreductase in a sample and the substrate in the reagent layer, and can include transferring electrons generated by the oxidation-reduction reaction to the second mediator via the first mediator, and causing the second mediator to accumulate (store) the transferred (received) electrons into the second mediator. In the present disclosure, the terms "perform incubation" and "store electrons" are used synonymously with each other in some cases. In the present disclosure, during incubation, the application of a voltage for measuring an electric signal is not substantially performed (e.g. it is not performed), in one or a plurality of embodiments.

In one or a plurality of embodiments, the time for the incubation after the contact between the sample and the reagent layer in the measuring method of the present disclosure is 1 minute or more, and with a view to accumulating a greater amount of electrons in the second mediator to increase an electric signal obtained, the incubation time is 2 minutes or more, 3 minutes or more, 4 minutes or more, 5 minutes or more, 6 minutes or more, 7 minutes or more, or 10 minutes or more. The upper limit of the incubation time is not particularly limited, and in one or a plurality of embodiments, examples of the incubation time include a period of time until all the substrate contained in the reagent layer is subjected to the oxidation-reduction reaction and electrons generated thereby are delivered. In one or a plurality of particularly non-limiting embodiments wherein the upper limit of the incubation time is not particularly limited, the incubation time is 30 minutes or less, 20 minutes or less, or 15 minutes or less. In one or a plurality of embodiments, the incubation time after the contact between the sample and the reagent layer in the measuring method of the present disclosure is 1 minute to 30 minutes, 2 minutes to 20 minutes, or 3 minutes to 15 minutes.

The incubation time in the measuring method of the present disclosure is preferably within a time range in which the substrate contained in the reagent layer is not exhausted by the reaction between the oxidoreductase as a target to be measured and the substrate, in one or a plurality of embodiments. The measuring method of the present disclosure, therefore, may include setting the incubation time within a time range in which the substrate contained in the reagent layer is not exhausted by the reaction between the substrate and the oxidoreductase as a target to be measured, in one or a plurality of embodiments.

In the present disclosure, the phrase of "such a time range that the substrate contained in the reagent layer is not exhausted by the reaction between the oxidoreductase as a target to be measured and the substrate" refers to a time range in which at least a proportion of the substrate contained in the reagent layer remains in a state of being able to react with an oxidoreductase, or a time range in which the substrate in a state of being able to react with an oxidoreductase is present in the reagent layer. In one or a plurality of embodiments, a time range in which the substrate is not exhausted can be predicted based on the content of the substrate contained in the reagent layer. In one or a plurality of embodiments, the time range in which the substrate is exhausted can be calculated based on the content of the substrate contained in the reagent layer.

In one or a plurality of embodiments of the measuring method of the present disclosure, the incubation after the contact between the sample and the reagent layer is preferably performed in a state in which no voltage is applied. In one or a plurality of embodiments of the measuring method of the present disclosure, it is preferable that no voltage is applied until the incubation for a predetermined time after the contact is finished.

The application of a voltage across electrodes can be performed by applying a constant voltage across electrodes (electrode pair), in one or a plurality of embodiments. The application of a voltage across electrodes can be performed by applying, to a working electrode, a voltage positive with respect to a counter electrode, in one or a plurality of particularly non-limiting embodiments. In one or a plurality of embodiments, the voltage applied to the working electrode is +50 mV to +500 mV, preferably +100 mV to +300 mV, +100 mV to +250 mV, or +100 mV to +200 mV, and more preferably +200 mV with respect to the counter electrode.

The measurement of an electric signal can be determined depending on the scheme used for measuring the amount of the oxidoreductase, in one or a plurality of embodiments.

When chronoamperometry is used to calculate the amount of an oxidoreductase, the measurement of an electric signal is performed by measuring a value of response current after a certain period of time has elapsed since a voltage is applied, in one or a plurality of embodiments. In one or a plurality of embodiments, the certain period of time is, for example, 20 seconds or less, 15 seconds or less, 10 seconds or less, 9 seconds or less, 8 seconds or less, 7 seconds or less, 6 seconds or less, 5 seconds or less, 4 seconds or less, 3 seconds or less, or 2 seconds or less, after the voltage application.

When chronocoulometry is used to calculate the amount of an oxidoreductase, the measurement of an electric signal is performed by chronologically measuring a value of response current to obtain an integrated value of the response current, in one or a plurality of embodiments. When cyclic voltammetry is used to calculate the amount of an oxidoreductase, the measurement of an electric signal is performed by continuously measuring a current value corresponding to a voltage during sweeping, to obtain a cyclic voltammetry waveform, in one or a plurality of embodiments.

In one or a plurality of embodiments, the calculation of the amount of the oxidoreductase based on an electric signal can be performed by a method such as chronoamperometry, chronocoulometry, and cyclic voltammetry. When chronoamperometry is used, the amount of a measurement object can be calculated by initially determining the relationship between the integrated value of a value of response current and the amount (concentration) of the measurement object (oxidoreductase) by a calibration curve or the like, and the integrated value of the measured value of response current to the calibration curve, in one or a plurality of embodiments.

The measuring method of the present disclosure may include applying a voltage for a short period of time (pre-application) immediately after the contact of the sample and the reagent layer, and measuring an electric signal generated by the application, in one or a plurality of embodiments. In one or a plurality of embodiments, the pre-application and the measurement of an electric signal generated by the pre-application enables adjustment of the incubation (electron storage) time depending on the amount of the oxidoreductase (measurement object) in a sample, which, for example, makes it possible to shorten the measurement time. In addition, it is possible to control an electric signal generated after the incubation (electron storage) so that it is within a predetermined range, which makes it possible to reduce loads on a measuring device.

The measuring method of the present disclosure, as another aspect, therefore includes: bringing a sample containing an oxidoreductase into contact with a reagent layer of a biosensor; applying a voltage across electrodes after the contact and before incubation (electron storage) (first application); measuring an electric signal generated by the first application (first measurement); calculating an incubation time based on the electric signal obtained by the first measurement; performing incubation for the incubation time determined by the calculation; applying a voltage across the electrodes after the incubation (second application); measuring an electric signal generated by the second application (second measurement); and calculating an amount of the oxidoreductase based on the electric signal obtained by the second measurement.

The first application (pre-application) in the measuring method of the present disclosure can be performed immediately after bringing a sample into contact with the reagent layer, in one or a plurality of embodiments. The first application (pre-application) is preferably performed at 0.01 to 10 seconds after the contact, or at 0.01 to 5 seconds after the contact, in one or a plurality of embodiments.

Application time in the first measurement (pre-measurement) in the measuring method of the present disclosure is preferably performed for about 0.01 seconds to 10 seconds, or about 0.01 seconds to 5 seconds, in one or a plurality of embodiments.

The measuring method of the present disclosure includes calculating an incubation time based on the electric signal obtained by the first measurement. The calculation (determination) of an incubation time can be performed based on an initially determined threshold value (value of the electric signal), in one or a plurality of embodiments. In one or a plurality of embodiments, the threshold value may be one, or two or more in number. The threshold value may be appropriately determined depending on the material of the electrodes, and the type of the mediators, in one or a plurality of embodiments.

In one or a plurality of non-limiting embodiments, in a case where three-level threshold values (high concentration, intermediate concentration, and low concentration) are set according to the concentration of the oxidoreductase, the incubation time can be determined as follows: when an electric signal (value of response current) obtained by the first measurement exceeds 2000 nA, which means the oxidoreductase has a high concentration, the incubation time can be determined to be 1 minute or less; when the electric signal (value of response current) is 1000 nA or more and 2000 nA or less, which means the oxidoreductase has an intermediate concentration, the incubation time can be determined to be more than 1 minute and less than 5 minutes (or for example, 3 minutes); and when the electric signal (value of response current) is less than 1000 nA, which means the oxidoreductase has a low concentration, the incubation time can be determined to be 5 minutes or more.

[Sample Containing Oxidoreductase]

A sample containing an oxidoreductase in the measuring method of the present disclosure may be a sample containing an oxidoreductase itself, or may be a sample containing a component converted into an oxidoreductase, in one or a plurality of embodiments. Examples of the sample include a biological specimen, in one or a plurality of embodiments. Examples of the biological specimen include blood, urine, and specimens derived from these, cell extract specimens, and cell culture solutions, in one or a plurality of embodiments. A sample containing an oxidoreductase is a sample for measurement of an amount of an oxidoreductase, and examples of the same include a sample that may contain an oxidoreductase, and a sample that may contain an oxidoreductase as a result of conversion of a component of the sample (that is suspected to contain an oxidoreductase), in one or a plurality of embodiments.

In the measuring method of the present disclosure, in one or a plurality of embodiments, an object to be analyzed (analysis object) such as hormone or a low-molecular-weight compound is converted into an oxidoreductase so that a "sample containing an oxidoreductase" is prepared, whereby the analysis object can be measured with a high sensitivity. According to the measuring method of the present disclosure, in one or a plurality of embodiments, measurement with a high sensitivity is enabled by converting an analysis object present in a trace amount concentration into an oxidoreductase.

Examples of the method for converting an analysis object into an oxidoreductase include a method using an oxidoreductase modified by a molecule recognition element (recognition-element-modified oxidoreductase) that releases, separates, or activates the oxidoreductase when it binds to the analysis object. An aptamer modified (labeled) with an oxidoreductase is one or a plurality of embodiments that binds to an analysis object thereby causing an oxidoreductase to be released, separated, or activated. By using it, for example, the measurement of the analysis object converted into an oxidoreductase is enabled. For example, by using a recognition-element-modified oxidoreductase that is immobilized on magnetic beads in a manner of being released from the magnetic beads when an analysis object binds thereto, an oxidoreductase corresponding to the analysis object can be released.

The measuring method of the present disclosure, therefore, may include converting an analysis object in a sample into an oxidoreductase, to prepare a sample containing the oxidoreductase, in one or a plurality of embodiments.

The measuring method of the present disclosure, in one or a plurality of embodiments, in a biosensor in which a second reagent layer containing a substance that can convert an analysis object in a sample into an oxidoreductase is arranged upstream to a first reagent layer, may include: introducing the sample containing an analysis object into the second reagent layer to prepare a sample containing an oxidoreductase; and bringing the prepared sample into contact with a reagent layer (the first reagent layer) containing a substrate of the oxidoreductase and mediators.

In one or a plurality of embodiments, examples of the analysis object include low-molecular-weight compounds, peptides, proteins, antigens, hormones, immune cells, rare cells, saccharides, toxins, virus particles, and metals. The measuring method of the present disclosure, therefore, in one or a plurality of embodiments, can be used in quantification of a low-molecular-weight compound, a peptide, a protein, an antigen, a hormone, an immune cell, a rare cell, a saccharide, a toxin, a virus particle, or a metal. The measuring method of the present disclosure, in one or a plurality of embodiments, is not used in measurement (for example, quantification) targeted to the substrate (for example, glucose, cholesterol, ethanol, sorbitol, fructose, cellobiose, lactic acid, and uric acid) of the oxidoreductase contained in the reagent layer of the biosensor used in the measurement.

Therefore the present disclosure relates to, as another aspect, a method for electrochemically measuring an analysis object in a sample using a biosensor. The biosensor used in the method of the present embodiment includes: a conductive part including two or more electrodes; a second reagent layer containing a substance that can convert the analysis object into an oxidoreductase; and a first reagent layer arranged in contact with the conductive part, wherein the first reagent layer and the second reagent layer are arranged in a flow channel, and the second reagent layer is positioned upstream to the first reagent layer. The first reagent layer includes a substrate of the oxidoreductase and two or more types of mediators, and the mediators include at least a first mediator and a second mediator, the first mediator being intended to transfer, to the second mediator, electrons generated by a reaction between the substrate and the oxidoreductase, the second mediator being intended to transfer, to the electrodes, the electrons transferred from the first mediator. The electrodes, the substrate, and the mediators in the biosensor of the present embodiment are as described above.

In one or a plurality of embodiments, the second reagent layer and the first reagent layer may be arranged in contact with each other, or may be arranged to be separated from each other.

The measuring method of the present disclosure, in one or a plurality of embodiments, can be performed in the same manner as that described above, except that a sample containing an analysis object is used as a sample, and the biosensor includes the second reagent layer containing a substance (for example, a molecule recognition element) that can convert the analysis object into an oxidoreductase.

[Biosensor Producing Method]

The biosensor of the present disclosure, in one or a plurality of embodiments, can be produced by preparing a base material in which a conductive part including two or more electrodes is formed, and mounting thereon a reagent layer including a substrate of an oxidoreductase and two or more types of mediators.

The reagent layer is mounted on at least a part of a working electrode among the two or more electrodes. The method for mounting the reagent is not limited particularly, and it can be performed by, for example, spotting a solution of the reagent on a part of the electrode, and drying the same. More specifically, the reagent layer can be formed by, for example, preparing a dispersion liquid in which the substrate of the oxidoreductase and the two or more types mediators, as well as a buffer and a binder as required are dispersed, dispensing the same on the electrodes, and drying the same.

In one or a plurality of embodiments, the biosensor of the present disclosure can be produced through a procedure shown in FIGS. 1A to 1E. In the present disclosure, however, the method for producing a biosensor is not limited to the following procedure.

As illustrated in FIG. 1A, an electrode system (conductive part) including a working electrode 12, a counter electrode 11, a reference electrode and detection electrode 13, and a detection electrode 14 was formed on a base material 10 by sputtering. As illustrated in FIGS. 1A to 1E, with the electrode system having the above-described configuration, the detection electrode 13 and the counter electrode 11 can detect the sample at the detection electrode 13, and further, the detection electrode 14 and the working electrode 12 can detect the sample at the detection electrode 14. This also makes it possible to calculate a period of time while incubation (electron storage) is performed, based on a timing when a sample is detected by the detection electrode 13 and a timing when a sample is detected by the detection electrode 14.

Figure 1B:
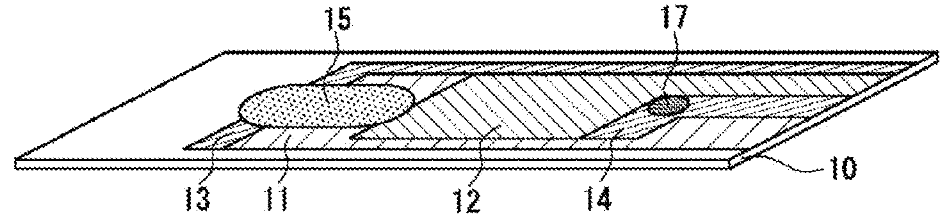

Next, the reagent layer 15 is formed. The reagent layer 15 may be mounted on at least a part of the working electrode 12, and as shown in FIG. 1B, the reagent layer 15 may be mounted so as to be in contact with a part of the detection electrode 13, the counter electrode 11, and the working electrode 12. The reagent layer 15 can be formed by: preparing a reagent liquid (dispersion liquid) that includes at least the substrate of the oxidoreductase and the two or more types of mediators, and in which a buffer and a binder are dispersed as required; mounting (dispensing) the reagent liquid on the detection electrode 13, the counter electrode 11, and the working electrode 12; and drying the same. In addition, a liquid sealing member 17 may be formed at a portion that is to be positioned at the end of a flow channel formed later (for example, on the detection electrode 14). The liquid sealing member 17 can be formed by applying a water stop reagent such as a water stop polymer and drying the same, in one or a plurality of embodiments. With this configuration, a sample brought into contact with the liquid sealing member 17 is gelated, whereby the sample is prevented from moving further downstream in the flow channel.

Figure 1C:
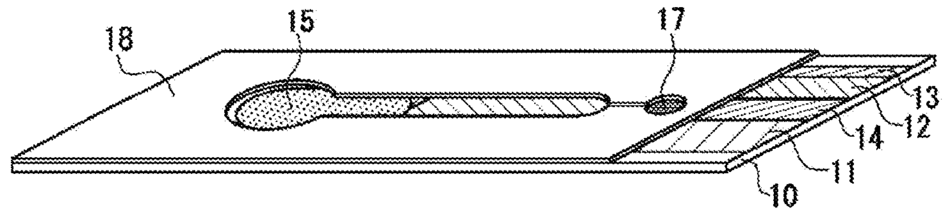

Next, as shown in FIG. 1C, a spacer 18 is arranged on the base material 10 on which the reagent layer 15 is mounted. The spacer 18 may be arranged with an insulating layer being interposed therebetween. The spacer 18 can be formed by using a resin film or tape, in one or a plurality of embodiments. The spacer 18 is arranged so as to allow the end parts of the electrodes to be exposed, the end parts being on one side where the liquid sealing member 17 is formed.

Figure 1D:
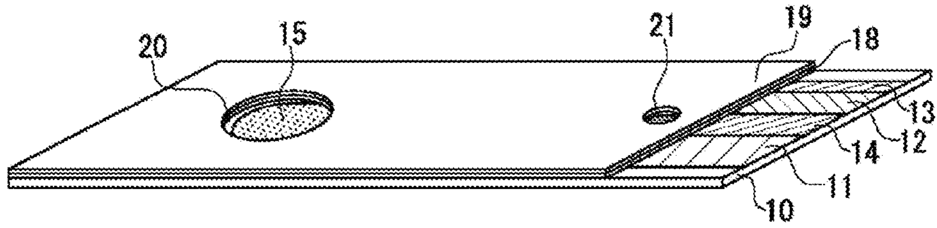
Figure 2:
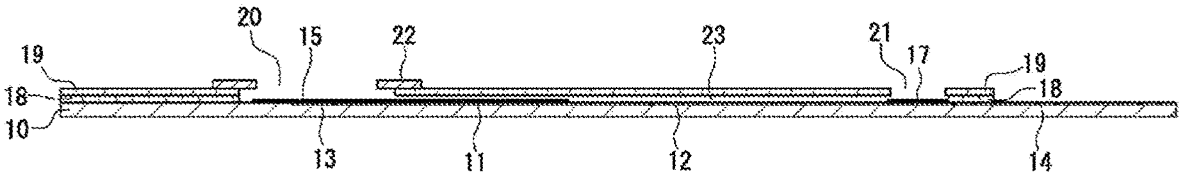
FIG. 2 is a cross-sectional view taken along line I-I in FIG. 1E.

Next, as shown in FIG. 1D, a cover 19 is arranged on the spacer 18. A space surrounded by the base material 10 and the cover 19, that is, a space in the opening of the spacer 18, functions as a flow channel. The cover 19 includes a through hole 20 serving as a sample supply part, and a through hole 21 serving as a vent. The through hole 20 serving as a sample supply part, and the through hole 21 serving as a vent, are formed so as to be positioned above the reagent layer 15 and the liquid sealing member 17, respectively. Examples of the material of the cover 19 include various types of plastic such as PET, in one or a plurality of embodiments. As shown in FIG. 2, a space (flow channel) 23 surrounded by the base material 10 and the cover 19 is formed, and a sample supplied to the through hole 20 serving as a sample supply part can move through the space (flow channel) 23 to the through hole 21 serving as a vent, via the reagent layer 15.

Figure 1E:
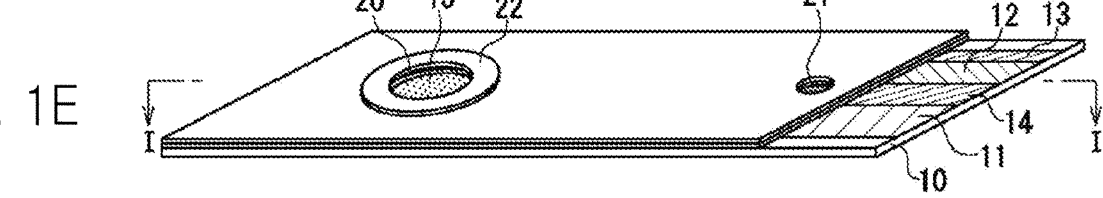

Finally, as shown in FIG. 1E, an O-ring-type water-repellent tape 22 is arranged so as to cover the periphery of the through hole 20 serving as a sample supply part of the cover 19. This makes it possible to prevent a sample from flowing out of the through hole 20 and the flow channel 23 (FIG. 2).

Figure 3A:
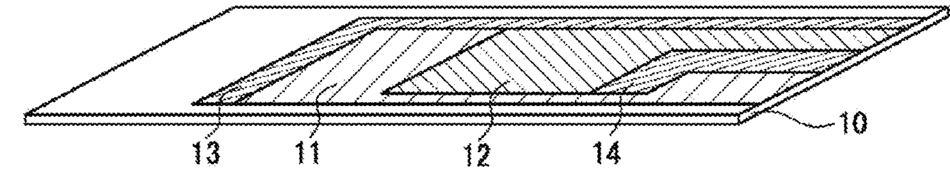
FIGS. 3A to 3E illustrate steps of an exemplary method for manufacturing a biosensor in one embodiment of the present disclosure, in which schematic diagrams of the biosensor in the steps are shown, respectively.
Figure 3B:
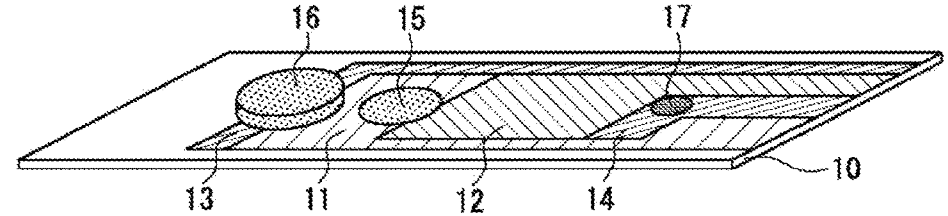
Figure 3C:
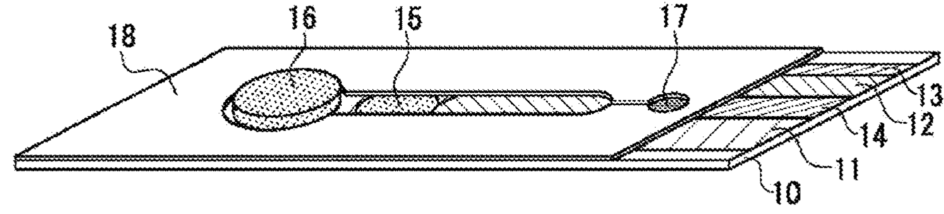
Figure 3D:
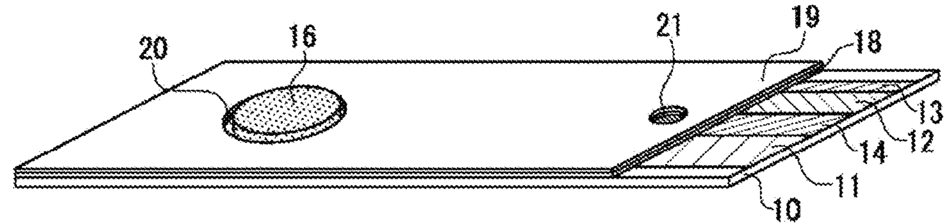
Figure 3E:
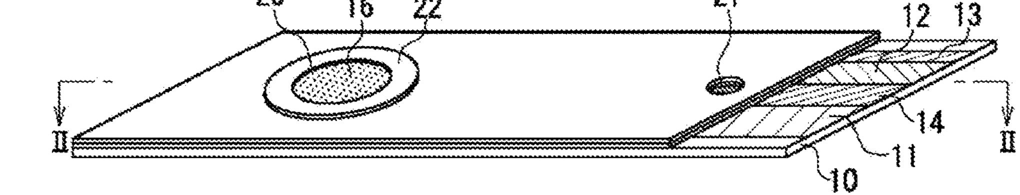
Figure 4:
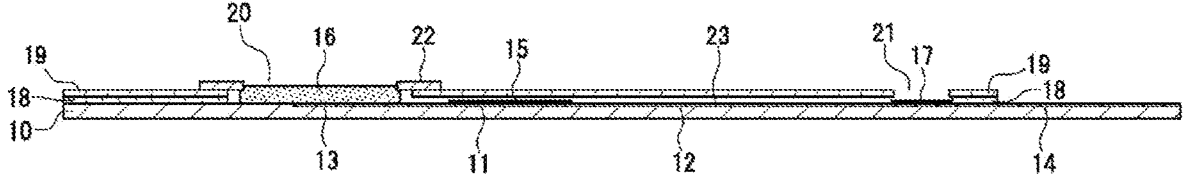
FIG. 4 is a cross-sectional view taken along line II-II in FIG. 3E.

FIGS. 3A to 3E and 4 show another example of the method for producing a biosensor according to the present disclosure. FIG. 4 is a cross-sectional view taken along line II-II in FIG. 3E.

In one or a plurality of embodiments, the biosensor of the present disclosure may include a first reagent layer 15 and a second reagent layer 16 as a reagent layer, as shown in FIGS. 3A to 3E and 4. The first reagent layer 15 includes at least a substrate of an oxidoreductase and two or more types of mediators, and the second reagent layer 16 includes a molecule recognition element modified by the oxidoreductase. By including the first reagent layer 15 and the second reagent layer 16 as is the case with the biosensor of the present embodiment, a period of time while a sample is passing through the second reagent layer can be adjusted according to the material of the second reagent layer, whereby the reaction period between the sample and the molecule recognition element can be varied appropriately, in one or a plurality of embodiments.

Besides, with a detection electrode 13 and a counter electrode 11, the presence of a sample at the detection electrode 13 can be detected. Besides, with a detection electrode 14 and a working electrode 12, the presence of a sample at the detection electrode 14 can be detected. A period of time while incubation (electron storage) is performed can be also calculated, based on a timing when a sample is detected by the detection electrode 13 and a timing when a sample is detected by the detection electrode 14.

As shown in FIG. 3B, the second reagent layer 16 is arranged so as to be in contact with the detection electrode 13 and the counter electrode 11. The first reagent layer 15 is arranged so as to be in contact with a part of the counter electrode 11 and the working electrode 12. The second reagent layer 16 can be formed by arranging a base material impregnated with a molecule recognition element modified by an oxidoreductase, on the detection electrode 13 and the counter electrode 11. In one or a plurality of embodiments, examples of the base material include a glass filter and a bead separation film. The first reagent layer 15 can be formed by: preparing a reagent liquid (dispersion liquid) that includes at least the substrate of the oxidoreductase and the two or more types of mediators, and in which a buffer and a binder are dispersed as required; arranging (dispensing) the reagent liquid on the counter electrode 11, and the working electrode 12; and drying the same.

The biosensor of the present embodiment can be produced in the same manner as that of the biosensor shown in FIGS. 1A to 1E, except that two reagent layers, i.e., the first reagent layer 15 and the second reagent layer 16, are formed.

The present disclosure may relate to one or a plurality of non-limiting embodiments described below:

[A1] A method for electrochemically measuring an amount of an oxidoreductase using a biosensor, wherein the biosensor includes a conductive part including two or more electrodes; and a reagent layer that is arranged in contact with the conductive part. The reagent layer includes a substrate of the oxidoreductase and two or more types of mediators. The mediators include a first mediator and a second mediator, wherein the first mediator is a mediator for transferring, to the second mediator, electrons generated by a reaction between the substrate and the oxidoreductase, and the second mediator is a mediator for transferring, to the electrodes, the electrons transferred from the first mediator. The method includes bringing a sample containing an oxidoreductase into contact with the reagent layer; performing incubation for a predetermined time after the contact, thereby causing the second mediator to accumulate the electrons; applying a voltage across the electrodes after the incubation; measuring an electric signal generated by the application of the voltage; and calculating an amount of the oxidoreductase based on the electric signal.

[A2] The method according to [A1] further including setting the incubation time within a time range in which the substrate contained in the reagent layer is not exhausted by the reaction between the substrate and the oxidoreductase as a target to be measured.

[A3] The method according to [A1] or [A2], wherein an amount of the substrate in the reagent layer (per 1 $cm^3$ of the reagent layer) is 4.4 nmol or more.

[A4] The method according to any one of [A1] to [A3], wherein the incubation time is 1 minute or more.

[A5] The method according to any one of [A1] to [A4], wherein the oxidoreductase is glucose dehydrogenase, and the substrate is glucose.

[A6] The method according to any one of [A1] to [A5], wherein the combination of the first mediator and the second mediator is the combination of 1-methoxy-5-ethylphenazinium ethylsulfate (1-mPES) and a ruthenium compound, or the combination of 1-methoxy-5-methylphenazinium methylsulfate (1-mPMS) and a ruthenium compound.

[A7] The method according to any one of [A1] to [A6], wherein the electric signal used in the calculation of the amount of the oxidoreductase is an electric signal measured within 10 seconds after the application.

[A8] The method according to any one of [A1] to [A7], wherein the biosensor includes a base material, and the conductive part and the reagent layer are formed on a surface of the base material.

[B1] A method for electrochemically measuring an amount of an oxidoreductase using a biosensor, wherein the biosensor includes a conductive part including two or more electrodes; and a reagent layer that includes a substrate of the oxidoreductase and two or more types of mediators, and is arranged in contact with the conductive part. The mediators include a first mediator and a second mediator. The first mediator is a mediator for transferring, to the second mediator, electrons generated by a reaction between the substrate and the oxidoreductase, and the second mediator is a mediator for transferring, to the electrodes, the electrons transferred from the first mediator. The method including bringing a sample containing the oxidoreductase into contact with the reagent layer of the biosensor; applying a voltage across the electrodes after the contact (first application); measuring an electric signal generated by the first application (first measurement); calculating an incubation time based on the electric signal obtained by the first measurement; performing incubation for the incubation time determined by the calculation; applying a voltage across the electrodes after the incubation (second application); measuring an electric signal generated by the second application (second measurement); and calculating an amount of the oxidoreductase based on the electric signal obtained by the second measurement.

[B2] The method according to [B1], wherein an amount of the substrate in the reagent layer (per 1 $cm^3$ of the reagent layer) is 4.4 nmol or more.

[B3] The method according to [B1] or [B2], wherein the oxidoreductase is glucose dehydrogenase, and the substrate is glucose.

[B4] The method according to any one of [B1] to [B3], wherein the combination of the first mediator and the second mediator is the combination of 1-methoxy-5-ethylphenazinium ethylsulfate (1-mPES) and a ruthenium compound, or the combination of 1-methoxy-5-methylphenazinium methylsulfate (1-mPMS) and a ruthenium compound.

[B5] The method according to any one of [B1] to [B4], wherein the electric signal obtained by the second measurement is an electric signal measured within 10 seconds after the application.

[B6] The method according to any one of [B1] to [B5], wherein the biosensor includes a base material, and the conductive part and the reagent layer are formed on a surface of the base material.

[C1] A biosensor for electrochemically measuring an oxidoreductase, the biosensor including a conductive part including two or more electrodes; and a reagent layer that includes a substrate of the oxidoreductase and two or more types of mediators, and is arranged in contact with the conductive part. The mediators include a first mediator and a second mediator. The first mediator is a mediator for transferring, to the second mediator, electrons generated by a reaction between the substrate and the oxidoreductase, and the second mediator is a mediator for transferring, to the electrodes, the electrons transferred from the first mediator. The biosensor is intended to be used in the measuring method according to any one of [A1] to [A6] and [B1].

[C2] A biosensor for electrochemically measuring an oxidoreductase, the biosensor including a base material; a conductive part including two or more electrodes formed on a surface of the base material; and a reagent layer that includes a substrate of the oxidoreductase and two or more types of mediators, and is arranged in contact with the conductive part. The mediators include at least a first mediator and a second mediator, the first mediator being intended to transfer, to the second mediator, electrons generated by a reaction between the substrate and the oxidoreductase, the second mediator being intended to transfer, to the electrodes, the electrons transferred from the first mediator.

[C3] The biosensor according to [C1] or [C2], wherein the oxidoreductase is glucose dehydrogenase, and the substrate is glucose.

[C4] The biosensor according to any one of [C1] to [C3], wherein the combination of the first mediator and the second mediator is the combination of 1-methoxy-5-ethylphenazinium ethylsulfate (1-mPES) and a ruthenium compound, or the combination of 1-methoxy-5-methylphenazinium methylsulfate (1-mPMS) and a ruthenium compound.

[C5] The biosensor according to any one of [C1] to [C4], wherein an amount of the substrate in the reagent layer (per 1 $cm^3$ of the reagent layer) is 4.4 nmol or more.

[C6] The biosensor according to any one of [C1] to [C5], wherein the first mediator is at least either one of 1-methoxy-5-ethylphenazinium ethylsulfate (1-mPES) and 1-methoxy-5-methylphenazinium methylsulfate (1-mPMS), and the second mediator is a ruthenium compound.

[D1] A method for electrochemically measuring an analysis object in a sample using a biosensor, wherein the biosensor includes: a conductive part including two or more electrodes; a second reagent layer containing an oxidoreductase modified by a molecule recognition element; and a first reagent layer that includes a substrate of the oxidoreductase and two or more types of mediators, and is arranged in contact with the conductive part. The mediators include a first mediator and a second mediator. The first mediator is intended to transfer, to the second mediator, electrons generated by a reaction between the substrate and the oxidoreductase, the second mediator is intended to transfer, to the electrodes, the electrons transferred from the first mediator, and the oxidoreductase modified by a molecule recognition element releases, separates, or activates the oxidoreductase when it binds to the analysis object. The method including: introducing the sample to the biosensor; performing incubation for a predetermined time, thereby causing the second mediator to accumulate the electrons; applying a voltage across the electrodes after the incubation; measuring an electric signal generated by the application of the voltage; and calculating an amount of the oxidoreductase based on the measured value.

[D2] The measuring method according to [D1] further including setting the incubation time within a time range in which the substrate contained in the first reagent layer is not exhausted by the reaction between the substrate and the oxidoreductase as a target to be measured.

[D3] The method according to [D1] or [D2], wherein an amount of the substrate in the first reagent layer (per 1 $cm^3$ of the reagent layer) is 4.4 nmol or more.

[D4] The method according to any one of [D1] to [D3], wherein the incubation time is 1 minute or more.

[D5] The method according to any one of [D1] to [D4], wherein the oxidoreductase is glucose dehydrogenase, and the substrate is glucose.

[D6] The method according to any one of [D1] to [D5], wherein the combination of the first mediator and the second mediator is the combination of 1-methoxy-5-ethylphenazinium ethylsulfate (1-mPES) and a ruthenium compound, or the combination of 1-methoxy-5-methylphenazinium methylsulfate (1-mPMS) and a ruthenium compound.

Hereinafter, although the following description describes the present disclosure in more detail by way of examples, these are illustrative, and the present disclosure is not limited to these examples.

EXAMPLE

In Experiment Examples, the following reagents and electrodes are used.

[Buffer]

0.5 M phosphate buffer (pH 7.3 to 7.4, 0.5 M NaCl, 0.25% Tween20)

[Mediator]

Ruthenium compound ($Ru(NH_3)_6Cl_3$, LT METAL CO., Ltd.)

1-mPES (1-methoxy-5-ethylphenazinium ethylsulfate, manufactured by Dojindo Laboratories Co., Ltd.)

[GDH]

FAD-dependent Glucose Dehydrogenase (product name: Glucose Dehydrogenase "Amano 8", MW: 180,000, manufactured by Amano Enzyme Inc.).

[Substrate]

Glucose

[Electrode]

DEP-CHIP (type name: DEP-ER-N, round gold electrode, Printed electrode for immobilization (three-electrode system), outer dimensions: 12.5 mm×4 mm×0.3 mm, working electrode area: 3.67 $mm^2$, manufactured by BioDevice Technology, Ltd.)

Experiment Example 1

By the following procedure, GDH was electrochemically measured.

<Procedure>

1. Dispensing the buffer, 50 μl each, into PCR tubes.
2. Dispensing 1 M Glucose, 50 μl each, into the tubes of Step 1.
3. Dispensing 5 mM 1-mPES, 50 μl each, into the tubes of Step 2.
4. Dispensing 500 mM Ru compound, 50 μl each, into the tubes of Step 3.
5. Dispensing a GDH solution, 50 μl each, into the tubes of Step 4 so that the final concentration was 0 to 12.5 nM, to obtain a reaction solution, and immersing the electrodes connected to a measuring device into the reaction solution.
6. Starting measuring the incubation time at a timing of the last operation of dispensing the GDH solution.
7. Applying a voltage across the electrodes five minutes after starting measuring the incubation time, and performing electrochemical measurement.

Applied voltage: 200 mV
Measuring time: 15 seconds
Sampling interval: 0.1 seconds 8. End of measurement.

The composition of the reaction solution (in the tubes of Step 6) was as follows.

<Composition of Reaction Solution>

Figure 5A:
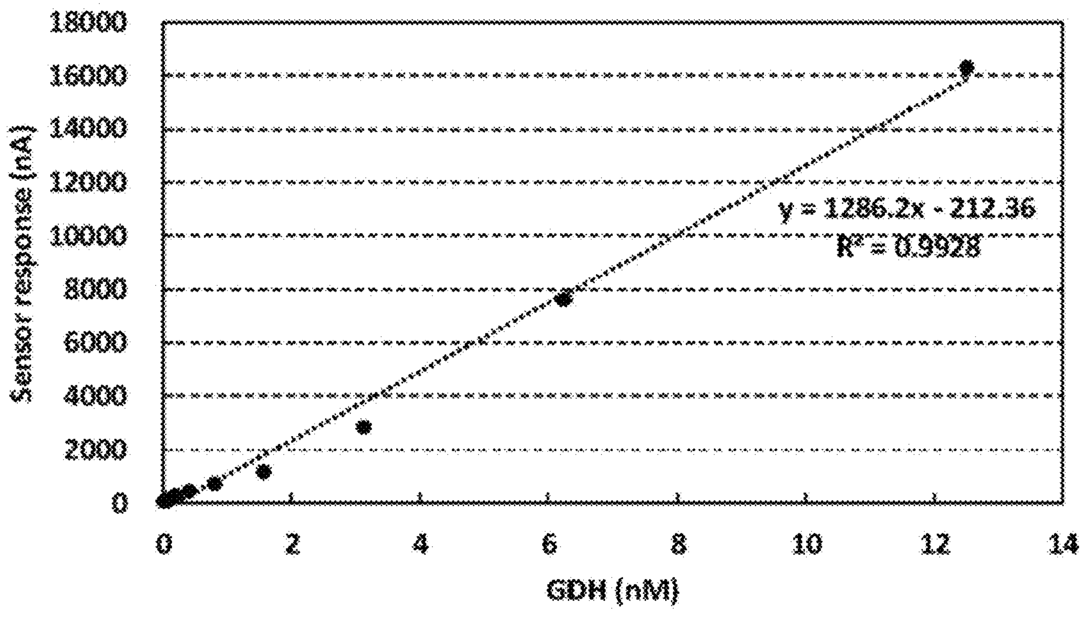
FIGS. 5A and 5B are graphs showing exemplary results of Experiment Example 1, and the graphs show results of evaluation of a concentration range of glucose oxidoreductase (GDH) that can be measured by performing a 5-minute incubation using a reaction solution that contains a substrate (glucose), mediators (1-methoxy-5-ethylphenazinium ethylsulfate (1-mPES) and a ruthenium compound) and that is prepared in such a manner that GDH has a final concentration of 0 to 12.5 nM.
Figure 5B:
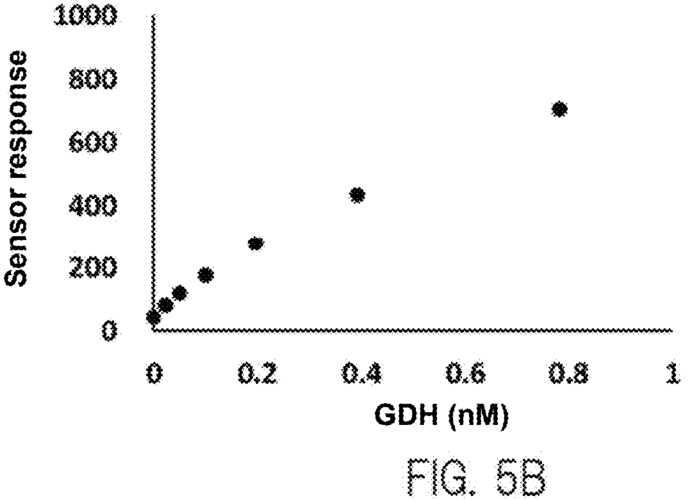

0.1 M phosphate buffer (pH 7.3 to 7.4)
0.1 M NaCl
0.05% Tween20
200 mM Glucose
1 mM 1-mPES 100 mM $Ru(NH_3)_6Cl_3$
0 to 12.5 nM GDH The obtained results are shown in FIGS. 5A and 5B. FIGS. 5A and 5B are graphs of response values at 2 seconds after the start of application of the voltage, and the low-concentration range part (0 to 0.8 nM) is expanded and shown in FIG. 5B. As shown in FIGS. 5A and 5B, the GDH concentration in the range of 0.024 nM (24 pM) to 12.5 nM could be detected by electrons stored during 5-minutes of incubation. In other words, 5-minute incubation (electron storage) enabled measurement of GDH in a pM order. With response values obtained at early timings after the application of the voltage (for example, at 2 seconds after the application of the voltage), quantification of GDH with high linearity was achieved.

Experiment Example 2

By the following procedure, GDH was electrochemically measured.

<Procedure>

1. Dispensing the buffer, 50 µl each, into PCR tubes.
2. Dispensing 1 M Glucose, 50 µl each, into the tubes of Step 1.
3. Dispensing 5 mM 1-mPES, 50 µl each, into the tubes of Step 2.
4. Dispensing 500 mM Ru compound, 50 µl each, into the tubes of Step 3.
5. Dispensing a GDH solution, 50 µl each, into the tubes of Step 4 so that the final concentrations were 0.56 nM, 5.56 nM, and 55.56 nM, to obtain a reaction solution, and immersing the electrodes connected to a measuring device into the reaction solution.
6. Starting measuring the incubation time at a timing of the last operation of dispensing the GDH solution.
7. Applying a voltage across the electrodes after a predetermined period of time (5 minutes, 10 minutes, or 15 minutes) has elapsed, and performing electrochemical measurement.

Applied voltage: 200 mV
Measuring time: 30 seconds
Sampling interval: 0.1 seconds 8. End of measurement.

The composition of the reaction solution (in the tubes of Step 6) was as follows.

<Composition of Reaction Solution>

0.1 M phosphate buffer (pH 7.3 to 7.4)
0.1 M NaCl
0.05% Tween20
200 mM Glucose
1 mM 1-mPES
100 mM $Ru(NH_3)_6Cl_3$
0.56 nM GDH, 5.56 nM GDH, 55.56 nM GDH The obtained results are shown in FIGS. 6A to 6C. FIGS. 6A to C show relative values (sensitivity ratios) with respective to a response value in a case where the incubation time is 5 minutes, which is assumed to be 100. As the response value, response values at 2 seconds after the start of application of the voltage were used. As shown in FIGS. 6A to 6C, at any GDH concentration, an increase in the response value depending on the incubation time was observed.

Experiment Example 3

By the following procedure, GDH was electrochemically measured.

<Procedure>

1. Dispensing the buffer, 50 µl each, into PCR tubes.
2. Dispensing Glucose, 50 µl each, into the tubes of Step 1 so that the final concentrations were 2 to 200 mM.
3. Dispensing 5 mM 1-mPES, 50 µl each, into the tubes of Step 2.
4. Dispensing 500 mM Ru compound, 50 µl each, into the tubes of Step 3.
5. Dispensing a 5 nM GDH solution, 50 µl each, into the tubes of Step 4, to obtain a reaction solution, and immersing the electrodes connected to a measuring device into the reaction solution.
6. Starting measuring the incubation time at a timing of the last operation of dispensing the GDH solution.
7. Applying a voltage across the electrodes after a predetermined period of time (5 minutes) has elapsed, and performing electrochemical measurement.

Applied voltage: 200 mV
Measuring time: 10 seconds
Sampling interval: 0.1 seconds 8. End of measurement.

The composition of the reaction solution (in the tubes of Step 6) was as follows.

<Composition of Reaction Solution>

Figure 7:
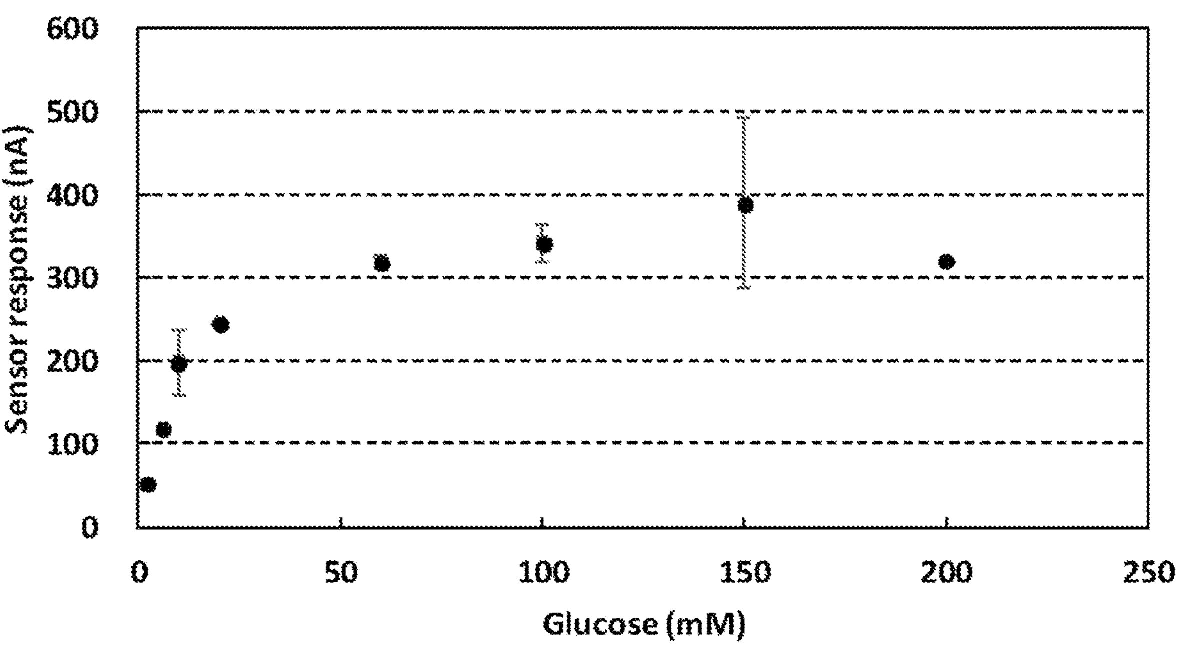
FIG. 7 is a graph showing exemplary results of Experiment Example 3, and the graph shows results of evaluation of the relationship between the concentration of a substrate in a reaction solution and a value of response current, by performing incubation for 5 minutes, using a reaction solution that contains a substrate (glucose, final concentration: 2 to 200 mM), mediators (1-mPES and a ruthenium compound), and GDH.

0.1 M phosphate buffer (pH 7.3 to 7.4)
0.1 M NaCl
0.05% Tween20
2 mM to 200 mM Glucose
1 mM 1-mPES
100 mM $Ru(NH_3)_6Cl_3$
1 nM GDH The obtained results are shown in FIG. 7. As the response value, response values at 2 seconds after the start of application of the voltage were used. As shown in FIG. 7, a high response current, higher than 200 nA, was obtained at a glucose concentration (substrate concentration) of 10 mM or more, under the conditions of the present Experiment Example. When the glucose concentration (substrate concentration) was 60 mM or more (60 to 200 mM), there was no change in the response values (no decrease in the response values was observed). In other words, even when the substrate (glucose) in the reaction solution had a high concentration (for example, when a substance serving as the substrate for the oxidoreductase reaction was contained at a high concentration in a biological sample), the concentration of the enzyme (GDH) could be measured, without the enzyme being subjected to substrate inhibition by glucose.

Experiment Example 4

By the following procedure, GDH was electrochemically measured.

Dispensing was performed so that the mediators in the reaction solution had concentrations shown in the table below.

<Procedure>

1. Dispensing the buffer, 50 µl each, into PCR tubes.
2. Dispensing 1 M Glucose, 50 µl each, into the tubes of Step 1.
3. Dispensing 5 mM 1-mPES, 50 µl each, into the tubes of Step 2 (dispensing the buffer into tubes that were to contain no 1-mPES).
4. Dispensing 500 mM Ru compound, 50 µl each, into the tubes of Step 3 (dispensing the buffer into tubes that were to contain no Ru compound).
5. Dispensing a GDH solution, 50 µl each, into the tubes of Step 4 so that the final concentrations were 0 to 10 nm, to obtain a reaction solution, and immersing the electrodes connected to a measuring device into the reaction solution.

6. Starting measuring the incubation time at a timing of the last operation of dispensing the GDH solution.
7. Applying a voltage across the electrodes after a predetermined period of time (5 minutes) has elapsed, and performing electrochemical measurement.

Applied voltage: 200 mV
Measuring time: 10 seconds
Sampling interval: 0.01 seconds
8. End of measurement.

The composition of the reaction solution (in the tubes of Step 6) was as follows.

<Composition of Reaction Solution>

0.1 M phosphate buffer (pH 7.3 to 7.4)
0.1 M NaCl
0.05% Tween20
200 mM Glucose
1-mPES, and $Ru(NH_3)_6Cl_3$, as shown in Table below.
0 to 10 nM GDH

TABLE 1

| | Concentration | |
|---|---|---|
| | 1-mPES | Ru compound |
| Mediator(—) | 0 mM | 0 mM |
| 1-mPES | 1 mM | 0 mM |
| Ru compound | 0 mM | 100 mM |
| 1-mPES + Ru compound | 1 mM | 100 mM |

Figure 8:
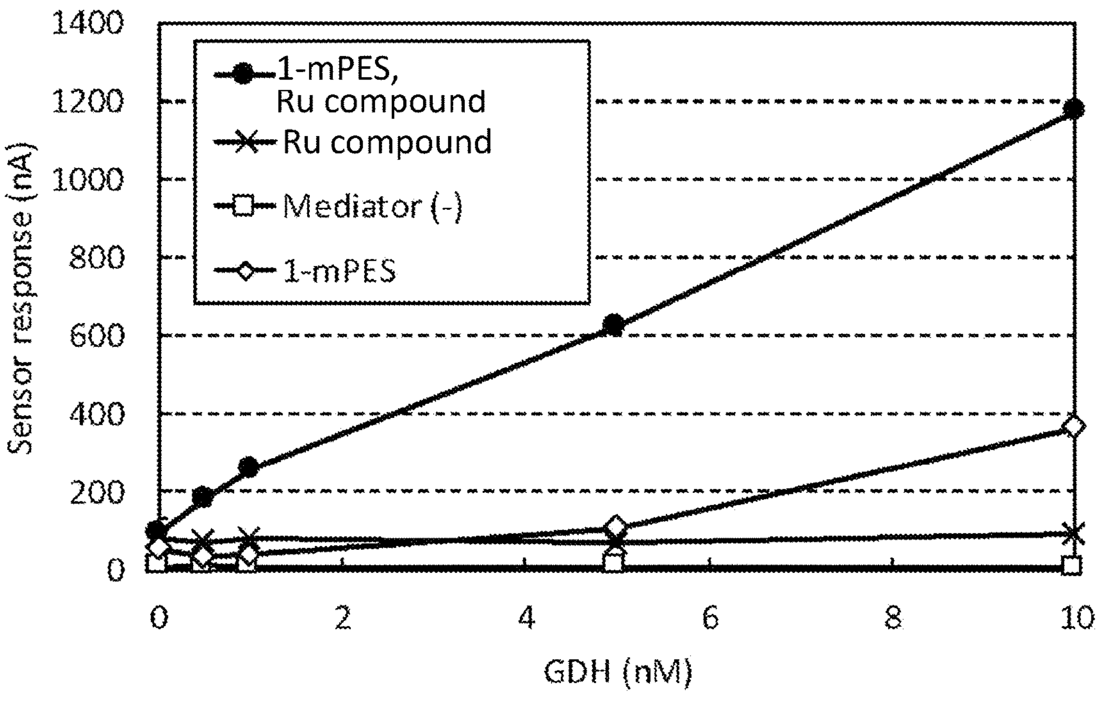
FIG. 8 is a graph showing exemplary results of Experiment Example 4, and the graph shows results of evaluation of the relationship between the types of mediators present in a reaction solution and a value of response current, by performing incubation for 5 minutes, using a reaction solution that contains a substrate (glucose), mediator(s) (1-mPES and/or a ruthenium compound), and GDH (final concentration: 0 to 10 nM).

The results are shown in FIG. 8. As the response values, mean values of response values at 2.0 to 2.1 seconds after the start of application of the voltage were used. As shown in FIG. 8, a sufficient response value could not be obtained with only one type of mediator. Particularly, when only a ruthenium compound was used, no response value was obtained at any GDH concentration. This is considered to be because the ruthenium compound received substantially no electrons from GDH, or was unable to store received electrons. In contrast, when two types of mediator (ruthenium compound and 1-mPES) were used, a high response value was obtained at any GDH concentration.

Experiment Example 5

By the following procedure, GDH was electrochemically measured.

<Procedure>

1. Dispensing the buffer, 50 μl each, into PCR tubes.
2. Dispensing 1 M Glucose, 50 μl each, into the tubes of Step 1.
3. Dispensing 5 mM 1-mPES, or 500 mM 1-mPES, 50 μl each, into the tubes of Step 2.
4. Dispensing 500 mM Ru compound, 50 μl each, into the tubes of Step 3.
5. Dispensing a 5 nM GDH solution, 50 μl each, into the tubes of Step 4, to obtain a reaction solution and immersing the electrodes connected to a measuring device into the reaction solution.
6. Starting measuring the incubation time at a timing of the last operation of dispensing the GDH solution.
7. Applying a voltage across the electrodes after a predetermined period of time (5 minutes) has elapsed, and performing electrochemical measurement.

Applied voltage: 200 mV
Measuring time: 10 seconds
Sampling interval: 0.01 seconds
8. End of measurement.

The composition of the reaction solution (in the tubes of Step 6) was as follows.

<Composition of Reaction Solution>

Figure 9:
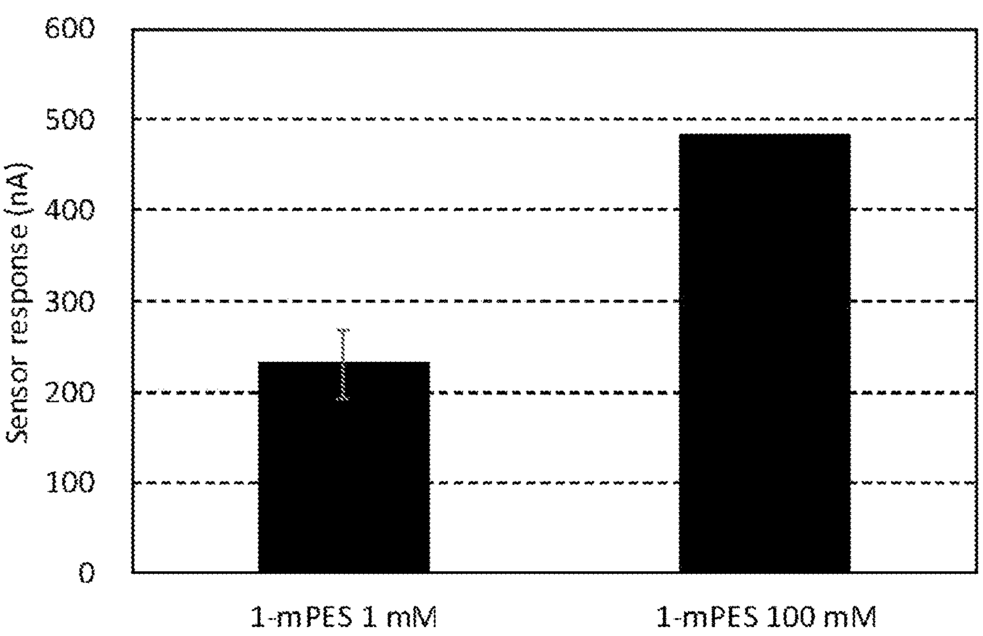
FIG. 9 is a graph showing exemplary results of Experiment Example 5, and the graph shows results of evaluation of the relationship between the concentration of 1-mPES in a reaction solution and a value of response current, by performing incubation for 5 minutes, using a reaction solution that contains a substrate (glucose), mediators (1-mPES and a ruthenium compound), and GDH.

0.1 M phosphate buffer (pH 7.3 to 7.4)
0.1 M NaCl
0.05% Tween20
200 mM Glucose
1 mM 1-mPES or 100 mM 1-mPES
100 mM $Ru(NH_3)_6Cl_3$
1 nM GDH The results are shown in FIG. 9. As the response values, mean values of response values at 2.0 to 2.1 seconds after the start of application of the voltage were used. As shown in FIG. 9, the sensitivity (response value) could be increased to double or more by increasing the amount of 1-mPES (first mediator) to 100 mM.

Experiment Example 6

Using adenosine DNA aptamer modified (labeled) GDH, GDH in a reaction solution was electrochemically measured by the following procedure.

The adenosine DNA aptamer is an aptamer that, as a target molecule recognition element, can recognize and bind with adenosine, is labeled with GDH, and is immobilized on magnetic beads. Without adenosine, the GDH is inactive. When adenosine binds to the aptamer, the GDH-labeled aptamer is released from the beads, and the GDH becomes active.

<Procedure>

1. Dispensing an adenosine DNA aptamer-immobilized beads, 100 μl each, into PCR tubes (final concentration: 6 μmol/100 μl).
2. Collecting the adenosine DNA aptamer-immobilized beads magnetically, and discharging liquid.
3. Dispensing an adenosine solution obtained by dissolving adenosine in a buffer, 120 l each, into the tubes of Step 2 (adenosine final concentration: 0 μM, 7.5 μM, 12.5 μM, 37.5 μM, 75 μM, 125 μM, 375 μM, or 750 μM).
4. Allowing a reaction to proceed for 5 minutes, then, collecting the beads (unreacted adenosine DNA aptamer-immobilized beads and beads with aptamer released) magnetically (2 minutes), and collecting supernatant.
5. Dispensing a buffer, 50 μl each, into PCR tubes.
6. Dispensing 1 M Glucose, 50 μl each, into the tubes of Step 5.
7. Dispensing 5 mM 1-mPES, 50 μl each, into the tubes of Step 6.
8. Dispensing 500 mM Ru compound, 50 μl each, into the tubes of Step 7.
9. Dispensing the supernatant obtained at Step 4 (containing the GDH-labeled aptamer released from the adenosine DNA aptamer-immobilized beads), 50 μl each, into the tubes of Step 8, and connecting the same to a measuring device.
10. Starting measuring the incubation time at a timing of the last operation of dispensing the supernatant obtained at Step 4.
11. Applying a voltage across the electrodes after a predetermined period of time (5 minutes) has elapsed, and performing electrochemical measurement.

Applied voltage: 200 mV

Measuring time: 10 seconds
Sampling interval: 0.01 seconds
12. End of measurement.

The composition of the reaction solution (in the tubes of Step 10) was as follows.

<Composition of Reaction Solution>
0.1 M phosphate buffer (pH 7.3 to 7.4)
0.1 M NaCl
0.05% Tween20
200 mM Glucose
1 mM 1-mPES
100 mM $Ru(NH_3)_6Cl_3$
GDH-labeled aptamer released from the magnetic beads (the adenosine DNA aptamer-immobilized beads) according to the adenosine concentration.

The measurement was carried in the same manner as that of the above-described procedure except that an adenosine solution obtained by dissolving adenosine in plasma in place of a buffer was used.

Figure 10:
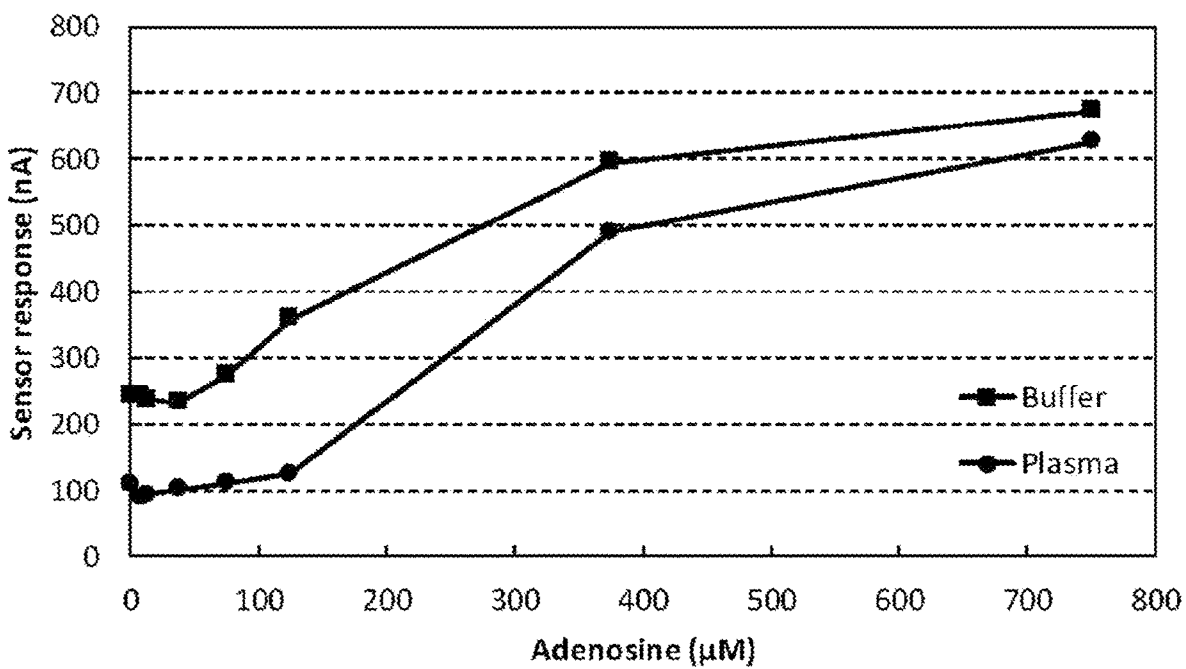
FIG. 10 is a graph showing exemplary results of Experiment Example 6, and that an adenosine DNA aptamer that can recognize and bind to adenosine and is labeled by GDH was used to cause a reaction with an analysis object (adenosine) in a sample, and a value of a response current generated by an oxidoreductase reaction of GDH separated from the GDH labeled adenosine DNA aptamer was measured, and it was confirmed to be possible to detect the analysis object (adenosine)

The results are shown in FIG. 10. As the response values, mean values of response values at 2.0 to 2.1 seconds after the start of application of the voltage were used. As shown in FIG. 10, increases in the response current depending on the concentration of the measurement object (adenosine) were confirmed, though differences are seen between the sensitivity in the case of the plasma and in the case of the buffer. In other words, a concentration of an analysis object was detected by using a GDH modified aptamer released due to a reaction between an aptamer and the analysis object (adenosine).

Experiment Example 7

By the following procedure, GDH was electrochemically measured.

[Production of Device]

Electrodes including counter electrodes, working electrodes, and reference electrode were produced on a PET base plate by sputtering a metal and trimming the same. Devices having a capillary structure were produced with use of the electrodes thus obtained.

<Procedure>
1. Dispensing the buffer, 50 μl each, into PCR tubes.
2. Dispensing 1 M Glucose, 50 μl each, into the tubes of Step 1.
3. Dispensing 5 mM 1-mPES, 50 μl each, into the tubes of Step 2.
4. Dispensing 500 mM Ru compound, 50 μl each, into the tubes of Step 3.
5. Dispensing GDH, 50 μl each, into the tubes of Step 4 so that the final concentrations were 0.56 nM, 5.56 nM, and 55.56 nM.
6. Sucking a part of the reaction solution from the tubes of Step 5 to one of the above-described devices, quickly after the dispensing (about 10 seconds after the dispensing).
7. Applying a voltage across the electrodes quickly after the sucking, and performing electrochemical measurement (first application and first measurement).

Applied voltage: 200 mV
Measuring time: 5 seconds
Sampling interval: 0.1 seconds 8. Applying a voltage across the electrodes after a predetermined incubation time (1, 3, or 5 minutes) has elapsed since the dispensing of Step 5, and performing electrochemical measurement (second application and second measurement).

Applied voltage: 200 mV
Measuring time: 15 seconds
Sampling interval: 0.1 seconds 9. End of measurement.

The composition of the reaction solution (in the tubes of Steps 7 and 8) was as follows.

Figures 11A, 11B:
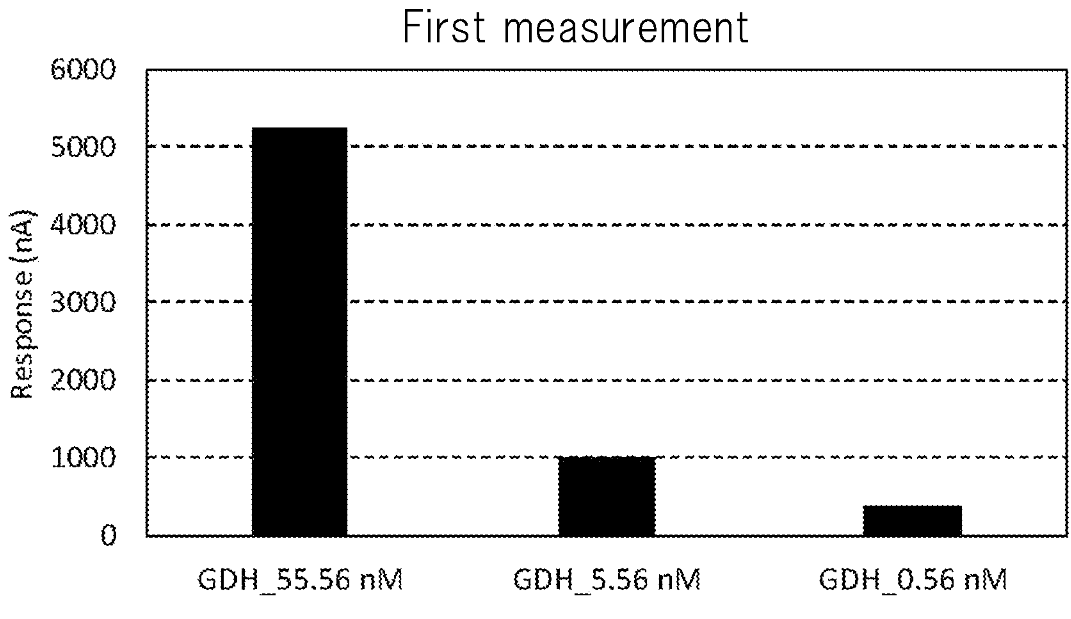
FIGS. 11A and 11B are graphs showing exemplary results of Experiment Example 7, and by performing the first application (pre-application), an incubation (electron storage) time was determined (calculated) for each measurement sample, incubation was performed for the incubation time thus calculated, and values of response current were determined.

<Composition of Reaction Solution>
0.1 M phosphate buffer (pH 7.3 to 7.4)
0.1 M NaCl
0.05% Tween20
200 mM Glucose
1 mM 1-mPES
100 mM $Ru(NH_3)_6Cl_3$
0.56 nM GDH, 5.56 nM GDH, and 55.56 nM GDH A part of the results is shown in FIGS. 11A and 11B. FIG. 11A shows results of measurement of response current values in the first measurement (at the pre-application), and FIG. 11B shows results of measurement of response current values in the second measurement. As the response values shown in FIG. 11A, response values at 0.5 seconds after the start of application of the voltage were used, and as the response values shown in FIG. 11B, response values at 2.0 seconds after the start of application of the voltage were used.

As shown in FIG. 11A, in the first measurement (pre-application), test samples (reaction solutions) having high GDH concentrations had high current values, while test samples (reaction solutions) having low GDH concentrations had low current values. The incubation (electron storage) time in the second measurement was varied depending on the current values in the first measurement. The results are shown in FIG. 11B. Current values of the test samples (reaction solutions) that had high current values (2000 nA or more at 0.5 seconds after the start of measurement) in the first measurement could be sufficiently measured after one-minute incubation (electron storage). In cases of current values of 1000 nA or more and less than 2000 nA at the pre-application, current values could be measured after three-minute incubation (electron storage). In cases of current values of less than 1000 nA in the first measurement, current values were at such a level that response values could be barely detected after five-minute incubation (electron storage). In other words, this suggests that, by initially setting threshold values and incubation (electron storage) times with respect to current values in the first measurement, respectively, and varying the incubation (electron storage) times by comparing the measured values in the first measurement and the threshold values, more rapid measurement was enabled, which could make it possible to reduce loads on devices and to reduce an area of a counter electrode in an electrode structure.

[Production of Biosensor]

A biosensor was produced through the following procedure as shown in FIGS. 3A to 3E.

As illustrated in FIG. 3A, by preparing a PET base plate 10 (length: 50 mm, width: 6 mm, thickness: 250 μm), sputtering a metal on one of the surfaces thereof, and trimming the same, a detection electrode 13, a counter electrode 11, a working electrode 12, as well as a reference electrode and detection electrode 14 were produced.

Next, as shown in FIG. 3B, on the base plate 10 on which the electrodes were formed, a first reagent layer 15, a second reagent layer 16, and a liquid sealing member 17 were provided. The second reagent layer 16 was provided on the detection electrode 13 and the counter electrode 11, so as to be in contact with the same. The first reagent layer 15 was provided on a part of the counter electrode 11 and the working electrode 12, so as to be in contact with the same. The liquid sealing member 17 was provided on the reference electrode and detection electrode 14. The second reagent layer 16 was formed by arranging a glass filter modified to contain a molecule recognition element modified by an oxidoreductase. The filter of the second reagent layer 16 had a diameter of 3 mm. The first reagent layer 15 was formed by arranging a reagent solution containing a substrate of the oxidoreductase, first mediator, second mediator, and a buffer, and drying the same. The liquid sealing member 17 was formed by arranging a polymer for sealing liquid.

Next, as shown in FIG. 3C, a spacer 18 having openings through which the second reagent layer 16, the first reagent layer 15, and the liquid sealing member 17 were exposed was arranged on the base plate 10 on which the second reagent layer 16, the first reagent layer 15, and the liquid sealing member 17 were formed. In addition, the spacer 18 was arranged so as to allow the end parts on one side (right side as viewed on FIG. 3C) of the electrodes to be exposed. The thickness of the spacer 18 was set to about 100 μm.

Next, as shown in FIG. 3D, a cover 19 having a through hole 20 serving as a sample supply part, and a through hole 21 serving as a vent, was arranged on the spacer 18. A space surrounded by the base plate 10 and the cover 19, that is, a space in the opening of the spacer 18, functions as a flow channel. The height of the flow channel was set to about 100 μm. The through hole 20 serving as a sample supply part and the through hole 21 serving as a vent were formed so as to be located above the second reagent layer 16 and the liquid sealing member 17, respectively. The through hole 20 serving as a sample supply part had a diameter of 4 mm, and the through hole 21 serving as a vent had a diameter of 0.5 mm.

Finally, as shown in FIG. 3E, an O-ring-type water-repellent tape 22 (inner diameter: 2 mm, outer diameter: 6 mm) was arranged on the cover 19. The water-repellent tape 22 is arranged so as to cover the periphery of the through hole 20 serving as the sample supply part, which makes it possible to prevent a sample from flowing out of the second reagent layer 16 (filter).

FIG. 4 is a cross-sectional view taken along line II-II in FIG. 3E. As shown in FIG. 4, a space (flow channel) 23 surrounded by the base plate 10 and the cover 19 is formed, and a sample supplied to the through hole 20 serving as a sample supply part can move through the space (flow channel) 23, via the second reagent layer 16 and the first reagent layer 15, to the through hole 21 serving as a vent.

The disclosure may be embodied in other forms without departing from the spirit or essential characteristics thereof. The embodiments disclosed in this application are to be considered in all respects as illustrative and not limiting. The scope of the disclosure is indicated by the appended claims rather than by the foregoing description, and all changes which come within the meaning and range of equivalency of the claims are intended to be embraced therein.

What is claimed is:

1. A method for electrochemically measuring an amount of an oxidoreductase using a biosensor, wherein the biosensor includes:

a conductive part including two or more electrodes; and a dry reagent layer that is arranged in contact with the conductive part, the reagent layer includes a substrate of the oxidoreductase and two or more types of mediators, the two or more mediators include a first mediator and a second mediator, the first mediator is a mediator for transferring, to the second mediator, electrons generated by a reaction between the substrate and the oxidoreductase, and the second mediator is a mediator for transferring, to the two or more electrodes, the electrons transferred from the first mediator, and the method comprises:

bringing a sample containing the oxidoreductase into contact with a flat surface of the dry reagent layer;

performing incubation for a predetermined time after the contact, thereby causing the second mediator to accumulate the electrons;

applying a voltage across the two or more electrodes after the incubation;

measuring an electric signal generated by the application of the voltage; and calculating the amount of the oxidoreductase based on the electric signal.

2. The method according to claim 1, further comprising:

setting the predetermined time for the incubation within a time range in which the substrate contained in the reagent layer is not exhausted by the reaction between the substrate and the oxidoreductase as a target to be measured.

3. The method according to claim 1, wherein an amount of the substrate in the reagent layer, per 1 $cm^3$ of the reagent layer, is 4.4 nmol or more.

4. The method according to claim 1, wherein the predetermined time for the incubation is 1 minute or more.

5. The method according to claim 1, wherein the oxidoreductase is glucose dehydrogenase, and the substrate is glucose.

6. The method according to claim 1, wherein the combination of the first mediator and the second mediator is a combination of 1-methoxy-5-ethylphenazinium ethylsulfate (1-mPES) and a ruthenium compound, or a combination of 1-methoxy-5-methylphenazinium methylsulfate (1-mPMS) and a ruthenium compound.

7. The method according to claim 1, wherein the electric signal used in the calculation of the amount of the oxidoreductase is an electric signal measured within 10 seconds after the application of the voltage.

8. A biosensor for electrochemically measuring an oxidoreductase, the biosensor comprising:

a base material;

a conductive part including two or more electrodes formed on a surface of the base material; and a reagent layer that includes a substrate of the oxidoreductase and two or more types of mediators, and is arranged in contact with the conductive part;

wherein the mediators include a first mediator and a second mediator, and the first mediator is a mediator for transferring, to the second mediator, electrons generated by a reaction between the substrate and the oxidoreductase, and the second mediator is a mediator for transferring, to the electrodes, the electrons transferred from the first mediator, and the measuring is a measurement performed by a measuring method comprising:

bringing a sample containing an oxidoreductase into contact with the reagent layer;

performing incubation for a predetermined time after the contact, thereby causing the second mediator to accumulate the electrons;

applying a voltage across the electrodes after the incubation;

measuring an electric signal generated by the application of the voltage; and calculating an amount of the oxidoreductase based on the electric signal.

9. The biosensor according to claim 8, wherein an amount of the substrate in the reagent layer, per 1 $cm^3$ of the reagent layer, is 4.4 nmol or more.

10. The biosensor according to claim 8, wherein the oxidoreductase is glucose dehydrogenase, and the substrate is glucose.

11. The biosensor according to claim 8, wherein the first mediator is at least either one of 1-methoxy-5-ethylphenazinium ethylsulfate (1-mPES) and 1-methoxy-5-methylphenazinium methylsulfate (1-mPMS), and the second mediator is a ruthenium compound.

12. A method for electrochemically measuring an amount of an oxidoreductase using a biosensor, wherein the biosensor includes:

a conductive part including two or more electrodes; and a reagent layer that includes a substrate of the oxidoreductase and two or more types of mediators, and is arranged in contact with the conductive part;

the mediators include a first mediator and a second mediator, wherein the first mediator is a mediator for transferring, to the second mediator, electrons generated by a reaction between the substrate and the oxidoreductase, and the second mediator is a mediator for transferring, to the electrodes, the electrons transferred from the first mediator, and the method comprises:

bringing a sample containing an oxidoreductase into contact with the reagent layer of the biosensor;

performing a first voltage application by applying a voltage across the electrodes after the contact;

performing a first measurement by measuring an electric signal generated by the first application;

calculating a time for incubation based on the electric signal obtained by the first measurement;

performing incubation for the incubation time determined by the calculation;

performing a second voltage application by applying a voltage across the electrodes after the incubation;

performing a second measurement by measuring an electric signal generated by the second application; and calculating an amount of the oxidoreductase based on the electric signal obtained by the second measurement.

* * * * *